(12) United States Patent
Hunter et al.

(10) Patent No.: US 8,814,874 B2
(45) Date of Patent: Aug. 26, 2014

(54) NAVIGATED CUT GUIDE FOR TOTAL KNEE RECONSTRUCTION

(75) Inventors: Mark W. Hunter, Broomfield, CO (US); Gordon Goodchild, Broomfield, CO (US); Brandon D. Larocque, Westminster, CO (US); Frank Strupeck, Boulder, CO (US); Scott Shaver, Thornton, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1318 days.

(21) Appl. No.: 11/706,145

(22) Filed: Feb. 13, 2007

(65) Prior Publication Data
US 2008/0195109 A1 Aug. 14, 2008

(51) Int. Cl.
*A61F 2/48* (2006.01)

(52) U.S. Cl.
USPC .......................................................... 606/87

(58) Field of Classification Search
USPC .............................................. 606/87, 88, 89
See application file for complete search history.

(56) References Cited

U.S. PATENT DOCUMENTS

| | | | |
|---|---|---|---|
| 4,117,796 A | 10/1978 | Strain | |
| 5,364,401 A * | 11/1994 | Ferrante et al. | 606/84 |
| 5,592,939 A | 1/1997 | Martinelli | |
| 5,681,316 A | 10/1997 | DeOrio et al. | |
| 5,740,808 A | 4/1998 | Panescu et al. | |
| 5,810,831 A * | 9/1998 | D'Antonio | 606/88 |
| 5,908,424 A * | 6/1999 | Bertin et al. | 606/88 |
| 5,911,723 A * | 6/1999 | Ashby et al. | 606/88 |
| 5,913,820 A | 6/1999 | Bladen et al. | |
| 5,984,930 A | 11/1999 | Maciunas et al. | |
| 6,381,485 B1 | 4/2002 | Hunter et al. | |
| 6,448,670 B1 | 9/2002 | Onodera et al. | |
| 6,474,341 B1 | 11/2002 | Hunter et al. | |
| 6,558,391 B2 * | 5/2003 | Axelson et al. | 606/88 |
| 6,561,856 B1 | 5/2003 | Gorshkov | |
| 6,676,662 B1 * | 1/2004 | Bagga et al. | 606/87 |
| 6,702,821 B2 | 3/2004 | Bonutti | |
| 6,711,431 B2 | 3/2004 | Pratt et al. | |
| 6,712,824 B2 * | 3/2004 | Millard et al. | 606/87 |
| 6,770,078 B2 * | 8/2004 | Bonutti | 606/88 |
| 6,932,823 B2 | 8/2005 | Grimm et al. | |
| 7,104,996 B2 | 9/2006 | Bonutti | |
| 7,241,298 B2 | 7/2007 | Nemec et al. | |

(Continued)

FOREIGN PATENT DOCUMENTS

| | | |
|---|---|---|
| EP | 1430842 | 6/2004 |
| FR | 2776176 | 9/1999 |
| FR | 2856274 | 12/2004 |

OTHER PUBLICATIONS

International Search Report and Written Opinion for PCT/US2008/001795 mailed Aug. 18, 2008, which claims the benefit of the current case, U.S. Appl. No. 11/706,145, filed Feb. 13, 2007.

*Primary Examiner* — Christopher Beccia
(74) *Attorney, Agent, or Firm* — Harness, Dickey

(57) ABSTRACT

A method and apparatus are disclosed that provides a system to perform a procedure on a patient or on a patient's anatomy. The apparatus can include a guide member that includes at least three degrees of freedom of movement of a guide or alignment portion. The apparatus can be used to guide or form reference points for a guide to resect a portion of an anatomy.

37 Claims, 11 Drawing Sheets

(56) References Cited

U.S. PATENT DOCUMENTS

| | | | |
|---|---|---|---|
| 7,488,324 B1* | 2/2009 | Metzger et al. | 606/89 |
| 7,520,880 B2* | 4/2009 | Claypool et al. | 606/88 |
| 2002/0029038 A1* | 3/2002 | Haines | 606/54 |
| 2002/0029045 A1 | 3/2002 | Bonutti | |
| 2002/0052606 A1 | 5/2002 | Bonutti | |
| 2002/0169460 A1 | 11/2002 | Foster et al. | |
| 2002/0173797 A1* | 11/2002 | Van Zile et al. | 606/88 |
| 2003/0028196 A1 | 2/2003 | Bonutti | |
| 2003/0069591 A1 | 4/2003 | Carson et al. | |
| 2004/0026242 A1 | 2/2004 | Marszal | |
| 2004/0102785 A1* | 5/2004 | Hodorek et al. | 606/87 |
| 2004/0122436 A1* | 6/2004 | Grimm | 606/87 |
| 2004/0172044 A1* | 9/2004 | Grimm et al. | 606/130 |
| 2004/0215071 A1 | 10/2004 | Frank et al. | |
| 2004/0236424 A1 | 11/2004 | Berez et al. | |
| 2005/0021039 A1* | 1/2005 | Cusick et al. | 606/88 |
| 2005/0085720 A1 | 4/2005 | Jascob et al. | |
| 2005/0149039 A1 | 7/2005 | Haines et al. | |
| 2005/0209598 A1 | 9/2005 | Grimm et al. | |
| 2005/0209605 A1 | 9/2005 | Grimm et al. | |
| 2005/0215888 A1 | 9/2005 | Grimm et al. | |
| 2005/0234461 A1 | 10/2005 | Burdulis et al. | |
| 2006/0030854 A1 | 2/2006 | Haines | |
| 2006/0036148 A1 | 2/2006 | Grimm | |
| 2006/0084867 A1 | 4/2006 | Tremblay et al. | |
| 2006/0122618 A1 | 6/2006 | Claypool et al. | |
| 2006/0155293 A1 | 7/2006 | McGinley et al. | |
| 2006/0190012 A1 | 8/2006 | Freitag | |
| 2006/0293681 A1 | 12/2006 | Claypool et al. | |

* cited by examiner

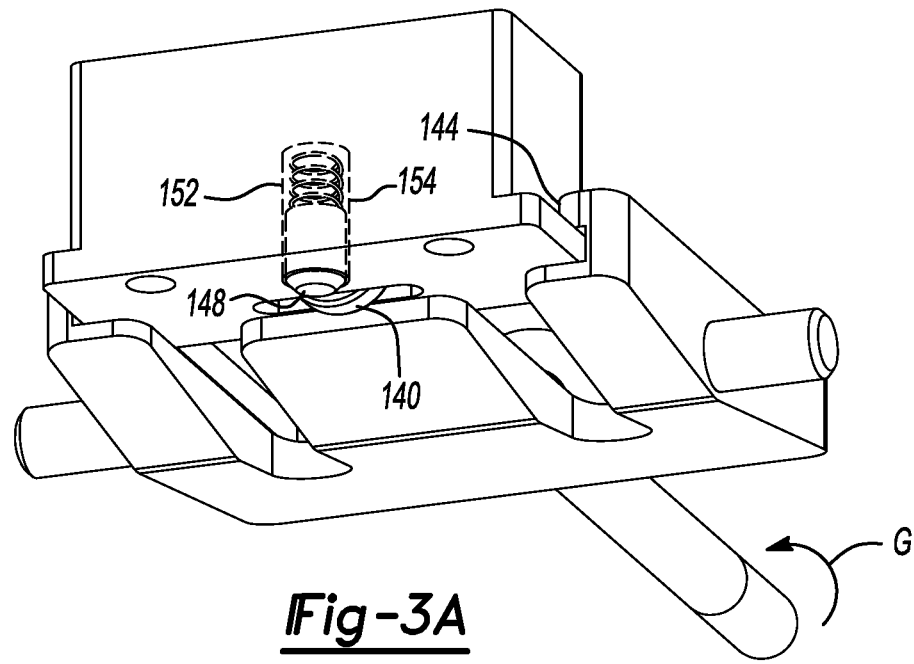
_Fig-3A_
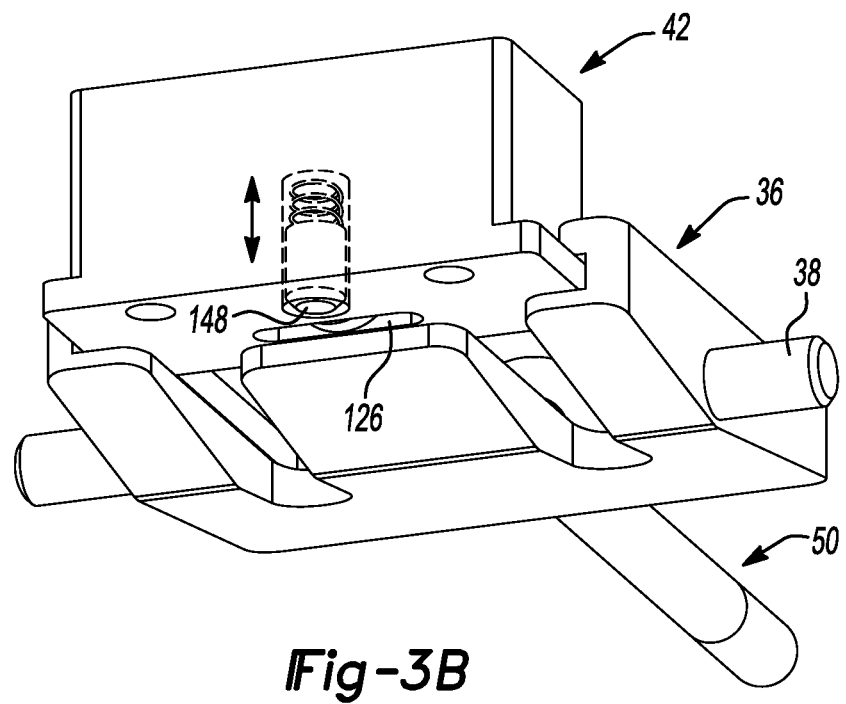
_Fig-3B_

NAVIGATED CUT GUIDE FOR TOTAL KNEE RECONSTRUCTION

FIELD

The present disclosure is related to an arthroplasty or orthopedic procedure, and in particularly to a navigated surgical procedure.

BACKGROUND

The statements in this section merely provide background information related to the present disclosure and may not constitute prior art.

An anatomy, such as the human anatomy, includes various portions that generally operate in a natural and efficient manner. For example, two bone portions can articulate or form an articulation between one another.

Portions of the anatomy, such as a joint or articulation can become damaged for various reasons. For example, disease or injury can damage a joint so that the articulation no longer occurs properly or is painful. A prosthesis, such as a knee joint replacement, hip joint replacement, or the like can be provided to replace the damaged or injured articulation portion.

Generally, an incision through the dermis or other soft tissue is required to obtain access to the bone structure defining the articulation. The incision through the soft tissue and the disruption of the soft tissues can require healing after the procedure is completed. It maybe desirable, therefore, to minimize the size of the incision and the disruption of the soft tissue. It may further be desirable to provide as much information as possible to a user, such as a surgeon, while performing a procedure. Therefore, it may be desirable to provide a navigation system and resection guide system that minimizes operative parts, maximizes flexibility, maximizes procedure information, and provides other benefits.

SUMMARY

Further areas of applicability will become apparent from the description provided herein. It should be understood that the description and specific examples are intended for purposes of illustration only and are not intended to limit the scope of the present disclosure.

A method and apparatus are disclosed that provides a system to perform a procedure on a patient or on a patient's anatomy. The apparatus can include a guide member or alignment member that includes at least three degrees of freedom of movement of a guide or alignment portion. The alignment member can be used to either guide a resection instrument or to guide the placement of a reference or datum point for a subsequently positioned cutting guide. The apparatus can also be used for placing the actual cutting device or developed with an integrated cutting device. The cutting device can include, but not limited to, ultrasonic cutting devices, blades, laser cutting devices, milling devices, rotary drill devices, and water jet cutting devices.

The apparatus can also be used with a navigation system to navigate or guide the guide portion relative to the anatomy. Navigation can assist a user in performing a procedure and can decrease the invasiveness of a procedure. The method can be applied to performing a procedure to assist in performing an efficient procedure and minimizing procedure time while maximizing repeatability and operative success.

The apparatus that allows the three degrees of freedom can include one or more plates that move relative to one another. Lock down or out features can lock down or out one or more of the plates to minimize or eliminate movement along one of the axes or degrees of freedom. The apparatus can be interconnected with a selected boney portion in a less invasive manner to minimize trauma to the soft tissue of the patient.

DRAWINGS

The drawings described herein are for illustration purposes only and are not intended to limit the scope of the present disclosure in any way.

FIG. 3A is a perspective view of a guide block with a locking portion in a locked position, according to various embodiments;

FIG. 3B is a perspective view of a guide block with a locking portion in an unlocked position, according to various embodiments;

DETAILED DESCRIPTION

The following description is merely exemplary in nature and is not intended to limit the present disclosure, application, or uses. Although the following description relates generally to a guide apparatus that can be navigated relative to a femur for performing a procedure on a knee, it will be understood that the guide apparatus can be used in any appropriate portion of the anatomy. For example, the guide apparatus can be used to guide or position any member relative to a distal or proximal portion of a tibia, a distal or proximal portion of a femur, a distal or proximal portion of a humerus, or any other appropriate bone portion. Moreover, the apparatus can be connected to any appropriate side of the bone portion, such as anterior, posterior, medial, lateral, etc. The guide apparatus can generally be positioned through a selected incision and positioned or navigated relative to the bone in an appropriate manner.

Figure 1:
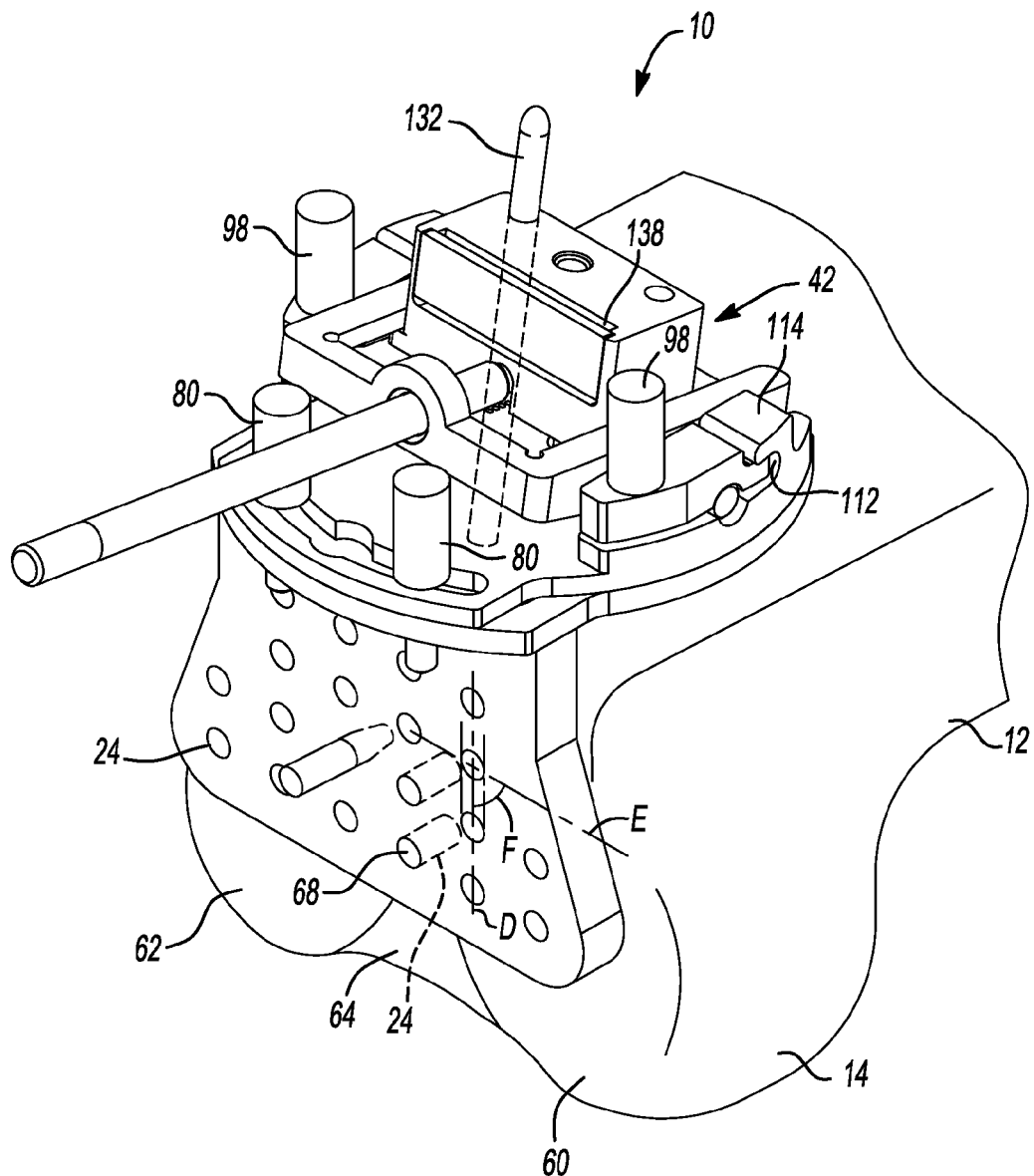
FIG. 1 is a perspective view of a guide apparatus according to various embodiments.
Figure 2:
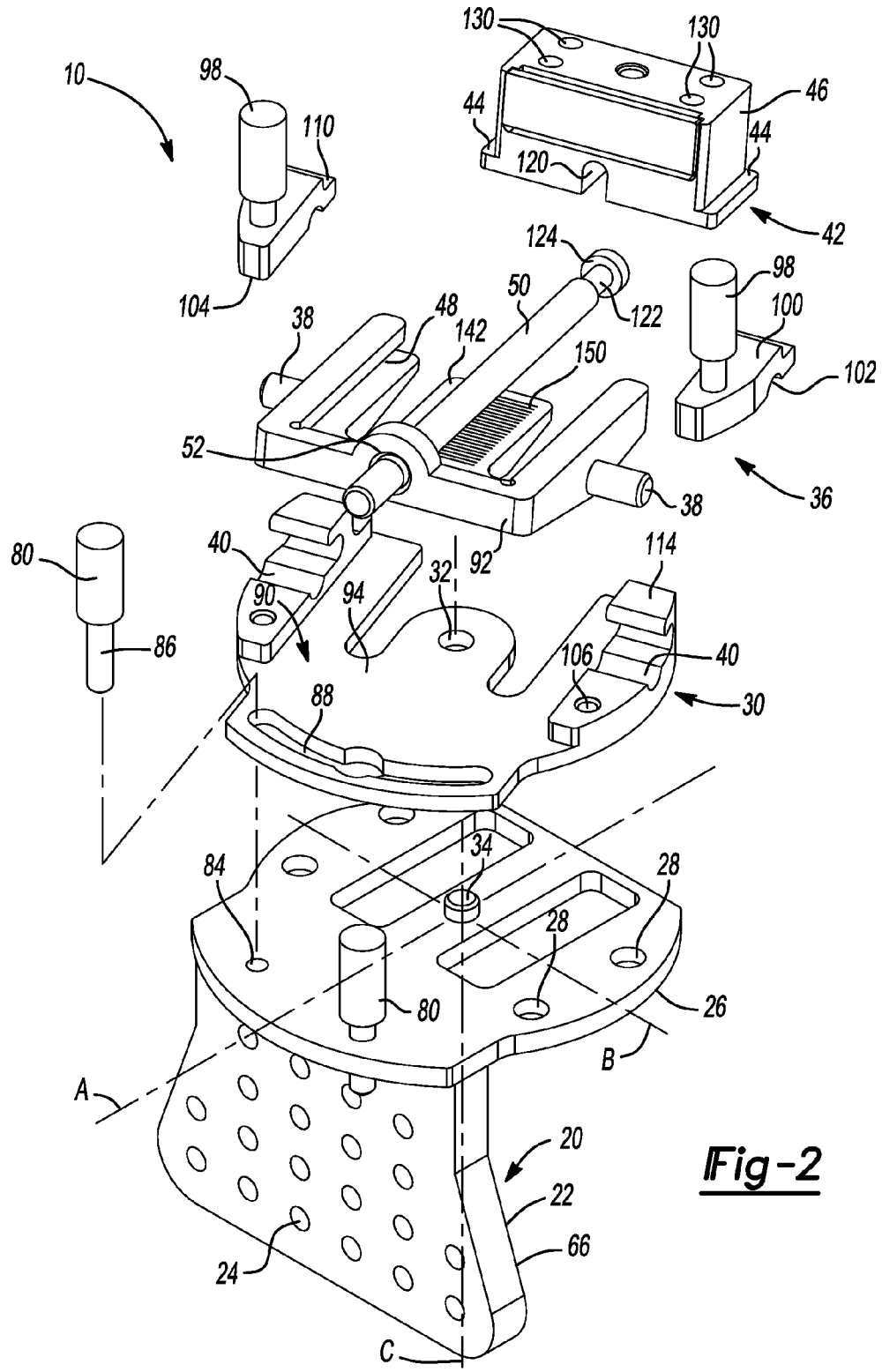
FIG. 2 is an exploded view of the guide apparatus of FIG. 1.

With reference to FIGS. 1 and 2, a navigated or trackable guide assembly 10 can be provided. The guide assembly 10 can be interconnected, for example, with a femur 12. According to various embodiments the guide assembly 10 can be interconnected with a distal end of the femur 14. The interconnection of the guide assembly 10 with the femur 12 will be discussed in more detail herein. Further, a trackable portion, such as a tracking device 500 or 600 can be interconnected with the guide assembly, as discussed herein. The tracking device can be used with a navigation system to navigate the guide apparatus 10. As discussed above, the guide apparatus is exemplary illustrated and discussed associated with the femur 12, but can also be associated or connected to a tibia, a humerus, a radius, or any other appropriate bone portion.

The guide assembly 10 can include a base or bone interconnection portion 20. The bone interconnection portion 20 can include a bone fixation arm or leg 22 through which can define a plurality of passages 24. As discussed herein, the bone fixation portion 22 can be attached to the bone via pins, screws, clamping mechanism, a cabling mechanism, or combinations of any of these. Extending from the bone fixation portion 22 is a bone contacting or guide member 26. The guiding member 26 can be provided in any appropriate angle relative to the bone fixation portion 22. For example, the guiding member 26 can be substantially orthogonal to the bone fixation portion 22. According to various embodiments, however, the bone fixation portion 22 can be eliminated and the guiding member 26 can define one or more fixation bores 28. The fixation bores 28 can be used to interconnect the guiding member 26 directly to a portion of the femur 12 or any other appropriate bone. Therefore, the discussion of the bone fixation portion 22 herein is merely exemplary.

The guide apparatus 10 can also include a first plate member 30. The first plate member 30 can interconnect with the guide member 26 in any appropriate manner. For example, the first plate 30 can define a passage or bore 32 which can cooperate or interact with a peg or extension 34 of the guide member 26.

The guide apparatus 10 can also include a second plate or rail portion 36. The rail portion 36 can interact with the guide member 26 through the first plate 30 by moving relative to the first plate 30 via extensions or dowels 38. The dowels 38 can articulate or move in a groove or depression 40 defined by the first plate.

The guide apparatus 10 can further include a navigated or tracked guide block or member 42. The guide block or member 42 can interact with the rail portion 36 via extension or slide members 44 that extend from a side wall 46 of the guide member 42. The extensions or fingers 44 can interact with a rail 48 defined by the rail portion 36.

A handle or joystick member 50 can extend from the guide block 42. The handle 50 can also extend through a passage or bore 52 defined by the rail portion. The handle 50 can be used to manipulate the guide block 42, as discussed further herein.

The guide apparatus 10 can be used to orient and move the guide block 42 in at least one degree of freedom relative to the guide member 26. As discussed further herein, the degrees of freedom of movement, which can include any appropriate number such as 2, 3, 4, etc., can also be relative to a portion of an anatomy, such as the femur 12.

For the clarity of the current discussion, a first axis A extends across the surface of the guide member 26. A second axis B can be provided substantially orthogonal to the first axis A. Briefly, the first axis A can provide a degree of freedom by sliding the guide block 42 along the track 48. The movement around axis B can include the movement of the dowel 38 within the groove 40 by rotating the rail portion 36 around the axis B. A third axis C can also be substantially orthogonal to the axes A or B and extend through the projection 34 and through the passage 32 in the first plate member 30. The first plate member 30, and the portions interconnected therewith, can then rotate about axis C.

The three axes A, B, and C of the guide apparatus 10 allow the alignment block 42 to move in at least three degrees of freedom. As discussed further herein, however, any one or more of the degrees of freedom can be eliminated from movement of the alignment block 42 relative to the guide member 26. By removing or preventing the movement along or relative to one of the degrees of freedom or axes, the alignment block 42 would be held or locked in that degree of freedom relative to the particular axis and relative to the associated anatomy, such as the femur 12.

With continuing reference to FIGS. 1 and 2, the various portions of the guide assembly 10 will be described in more detail. The bone fixation portion 22 that defines the plurality of passages 24 can be used to affix the bone fixation portion 22 relative to any appropriate portion of the anatomy, such as the femur 12. As exemplary illustrated in FIG. 1, the bone fixation portion 22 can be placed against a distal portion 14 of the femur 12. The distal portion 14 of the femur 12 can include various anatomical portions or features, such as condyles. The distal portion of the femur 14 can generally define a first condyle 60 and a second condyle 62. The first and second condyles 60, 62 can be the medial and lateral condyles. The identity of a particular condyle, however, is anatomy specific. Between the two condyles 60, 62 is an intercondylar path or notch 64.

The bone fixation portion 22 can define a bone contacting surface 66 that can contact the bone portion or the condyles 60, 62. The bone contacting surface 66 or the bone fixation portion 22 can be formed of a substantially rigid material and formed along a plane. Therefore, the bone contacting surface 66 can define a plane that can contact points defined by the condyles 60, 62 that are coplanar. Therefore, the bone contacting surface 66 of the bone fixation portion 22 can be used to define a plane of the distal portion 14 of the femur 12.

Briefly, as discussed further herein, a tracking device, according to various embodiments, can be interconnected with the guide apparatus 10. The tracking device can be tracked to determine the position of the guide apparatus 10 relative to the anatomy. Because the guide apparatus can be used to contact coplanar points on the anatomy, such as the femur 12, it can be used to track or determine a plane in the anatomy.

The bone fixation portion 22 can be used to fix the guide apparatus 10 relative to the femur 12. Various fixation members, such as fixation pins 68 can be driven through one or more of the passages 24 to fix the guide apparatus 10 to the femur 12. It will be understood that any appropriate number of the fixation pins can be used to affix the guide apparatus 10 to the femur 12. Further, it will be understood that any other appropriate fixation portion can be provided. For example, an intramedullary rod can be passed along the intramedullary canal of the femur 12 to fix the guide apparatus 10 to the femur 12. The intramedullary rod could extend from the bone fixation portion 22 into the femur 12. The fixation pins, however, can be the sole means of fixation of the guide apparatus 10 to the femur 12. As discussed above, the fixation passages 28 can also be used, either alternatively or in addition to the passages 24, to fix the guide apparatus 10 to the femur 12.

The fixation passages 24 can be provided in a plurality of configurations. For example, a substantially Euclidian based grid pattern can be used to define points for positioning the passages 24. Alternately, various curve configurations, polygonal configurations, or the like of the passages 24 can be provided.

These multiple configurations can be provided at various calibrated orientations. For example, either the substantially square configuration of the passages 24, as illustrated in FIG. 1, or a curve configuration of the passages 24 can be used to move the guide apparatus 10 relative to the femur by removing the guide apparatus 10 from the femur and repositioning it on previously positioned fixation pins 68. For example, the passages 24 can be provided at five millimeters apart. Therefore, driving the fixation pin 68 through a first set of selected passages 24 and then repositioning the guide apparatus 10 on a second set of the passages 24 one position relative to the first set of guide passages 24 can move the entire guide apparatus five millimeters, thereby moving the guide block 42 the same five millimeters. A curved configuration can allow for a rotation of the guide apparatus 10 a similar amount. In addition, any other appropriate configuration can also provide to move the entire apparatus 10 a selected amount relative to the anatomy. This type of passage configuration can reduce or eliminated additional holes in the bone or the need to create additional holes.

In addition, the passages 24 can be provided at angles relative to the bone contacting surface 66 or the bone fixation portion 22 and relative to other of the passages 24. The passages 24 can include an acute angle defined between axis D of the passage 24 and a line E on the plane defined by the bone contacting surface 66. An angle F between these two lines can be any appropriate angle, such as an acute or obtuse angle. Other of the passages 24 can be provided substantially orthogonal to the plane or line E.

When a plurality of the fixation pins 68 are driven through a plurality of the passages 24 to engage the femur 12 along both the angled passage and straight passages, the guide apparatus 10 would be held or immobilized relative to the femur 12. The angle formed between the plurality of the pins 68, such as converging or diverging, does not allow the guide apparatus 10 to slide off or move off of the femur 12 along the two converging or diverging angled paths of the passages 24.

Alternatively, the passages 24 can be orthogonal to the line E and the plane of the bone contacting surface 66. The fixation pin 68 can include an engagement or cooperation portion to hold the guide apparatus 10 to the bone 12. Therefore, the fixation pin 68 can be driven into the bone 12 in any appropriate manner and the passages 24 can be provided, in any appropriate manner to fix the guide apparatus 10 to the bone 12.

The guide surface or member 26 can be positioned relative to a second portion of the femur 12, such as an anterior surface thereof. It will be understood, as discussed above, that the guide apparatus 10 can be interconnected with any appropriate portion of the anatomy. Therefore, the guide member 26 can be positioned on the medial, lateral, or posterior surface of the femur 12, on a proximal surface on a tibia, or any other appropriate surface. Thus, the guide apparatus 10 can be used when connected to any appropriate portion of the bone. This can also allow a cutting guide 650 (FIG. 10) to be positioned on any appropriate portion or side of a bone portion. The guide member 26 can also define a plane that rests upon the bone, such as the femur 12. As discussed further herein, the planes or surfaces of the bone fixation portion 22 and the guide portion 26 can be used for navigation or determination of positions of portions of the guide apparatus 10.

The guide member 26 can assist in defining or forming the mechanisms that allow the movement of the various portions relative to the guide member 26. For example, the guide member 26 can include the projection 34. The projection 34 that can extend through the passage 32 in the first plate 30 and can allow the first plate 30 to rotate about or around axis C on the guide member 26.

The rotation of the first plate 30 on the guide member 26 can be limited by lockout or friction screws 80. The screws 80 can pass through a movement track 88 defined by the first plate 30 and interconnect with a bore or connection portion 84 in the guide plate 26. The lockout screws 80 can be provided in any appropriate number and two lockout screws 80 are merely exemplary. The lockout screws 80 can compress the first plate 30 onto the guide member 26. By compressing the first plate 30 onto the guide member 26, a friction interaction can be created to eliminate movement of the first plate 30 relative to the guide plate 26.

The lockout screws can include a threaded connection portion 86 that can cooperate with a thread in the bore 84. It will be understood, however, that any other appropriate interconnection can be provided, such as a twist lock, quarter turn lock, or the like. Therefore the lockout screws 80 can either progressively tighten against the first plate 30 to restrict its movement relative to the guide member 26 or can have a first lock and a second unlocked orientation.

When the lockout screws 80 are not locking the first plate 30 relative to the guide member 26 the lockout screws 80 can provide a guide portion relative to which the first plate 30 can translate. The lockout screws 80 can pass through the track 88 so that the track 88 can allow the first plate 30 to move relative to the lockout screws 80.

The track 88 can define any appropriate amount of movement of the first plate 30 relative to the fixation member 26. For example, the track 88 can define about zero to about 360 degrees of rotation of the first plate 30 relative to the guide member 26. It will be understood, according to various embodiments, that the track 88 can define about one degree to about thirty degrees of rotation around the axis C relative to the guide member 26.

The rail portion 36, which includes the dowels 38, can be positioned relative to the first plate 30. The rail portion can ride or slide on a top surface 90 of the first plate 30. The top surface 90 of the first plate 30 can be provided to allow movement of the rail portion 36 relative to the first plate 30 by rotating around axis B.

The dowel members 38, positioned within the grooves 40, can allow the rail portion to tilt or rotate around axis B. In other words, a front portion 92 of the rail portion 36 can be tilted relative to a front portion 94 of the first plate 30. For example, the rail portion 36 can be positioned between the front portion 92 resting on the front portion 94 of the first plate 30 and the front portion 92 of the rail portion 36 lifted so that there is space between the front portion 92 of the rail portion and the front portion 94 of the first plate 30.

A second set of lock out or down constriction screws 98 can be provided to cooperate with the first plate to resist or lock the rail portion 36 relative to the first plate in a selected orientation. The second set of lockout screws 98 can interconnect with a constriction or lockout member 100 that includes a second rail groove 102. The second rail groove 102 can cooperate with the first rail groove 40 in the first plate 30 to define a passage for the dowel or finger 38.

The lockout portion 100 can include a forward portion 104 that defines a passage to allow the second set of lockout screws 98 to pass through and interconnect with a lockout screw passage 106 in the first plate 30. The second set of lockout screws 98 can be substantially similar to the first set of lockout screws 80. Therefore, the passage 106 can be threaded, include a twist lock, or any other appropriate lock portion.

The rear portion of the lockout member 100 can include a rear finger 110. The rear finger 110 can fit in a slot 112 defined by a raised finger 114 of the first plate 30. The rear portion 110 can rotate in the slot 112 by movement of the lockout screw 98 relative to the passage 106 in the first plate 30.

As discussed above, the rail portion 36 can rotate about the axis B to be tilted or rotated relative to the first plate 30. The lockout screw 98 can be used to lockout or resist movement of the rail portion 36 by compressing against the dowels 38 by moving the lockout finger or member 100 to compress the dowel 38 relative to the first groove 40. A friction interaction can then be created to resist or eliminate movement of the rail portion 36 relative to the first plate 30.

The alignment block 42, as discussed above, can include the projection or rail interaction fingers 44. The rail 48, defined by the rail portion 36, can guide or hold the alignment block 42 relative to the rail portion 36. The alignment block 42 can be moved along the rail 48 with the handle 50. The handle 50 can be interconnected with the alignment block 42 in any appropriate manner. For example, the alignment block 42 can define a passage or groove 120 which can fit over a recessed or depressed portion 122 of the handle 50. An enlarged knob 124 can then interact with an interior slot 126 defined by the alignment block 42.

Movement of the handle 50 along the axis A can move the alignment block 42 relative to the rail portion 36. The axis A, illustrated relative to the guide member 26, can be generally defined along the longitudinal axis of the rail 48 or the handle 50. Thus, the alignment block 42 can move along the rail 48.

The alignment block 42 can define various portions. For example, the alignment block 42 can define passages or through bores 130 in any appropriate configuration. For example, the through bores 130 can be positioned at the corners of the alignment block 42, at the center of the alignment block 42, or at any appropriate location. The bores 130 can be positioned in various orientations, similar to the passages 24, to allow the alignment block to define a plurality of configurations for guiding a drill or alignment pins 132.

As will be discussed further herein, the passages 130 can be used to guide a fixation pin 132 into a selected portion, such as the femur 12, or a drill portion. One or more of the guide fixation pins 132 can be driven through the alignment block 42. As discussed herein the alignment block 42 can be aligned relative to the femur 12 and the fixation pins 132 driven through the alignment block 42 and into the bone 12. Alternatively, the passages 130 can be used to guide only a drill bit. The drill bit can form reference bores in the bone to receive the alignment pins after the guide apparatus 10 is removed.

The guide apparatus 10 can be removed from the bone 12 and a second guide apparatus can be positioned relative to the fixation pins 132 to guide a resection instrument relative to the bone 12. As illustrated herein, FIG. 10, the resection guide can be held in place wit the alignment pins 132. The pins 132 can be positioned though the passages 130 or can be placed in the bores formed in the bone with the alignment block 42 and the passages 130.

The alignment block 142 can also define a slot or passage 138. The slot 138 can be provided for various purposes. According to various embodiments, the slot 138 can be used to guide a resection instrument relative to the bone 12 (FIG. 10). According to various embodiments, the slot 138 can also be used to receive or interconnect with a tracking device (FIG. 9) as discussed further herein. The interconnected and tracking device can include that disclosed in U.S. patent application Ser. No. 10/941,782, filed on Sep. 15, 2004, and entitled "METHOD AND APPARATUS FOR SURGICAL NAVIGATION," or U.S. patent application Ser. No. 11/241,837, filed on Sep. 30, 2005, entitled, "METHOD AND APPARATUS FOR SURGICAL NAVIGATION," both incorporated herein by reference.

The alignment block 42 can be moved relative to the rail portion 36, as discussed above, and held relative thereto. In addition to the locking members, discussed above, the alignment block can also be held relative to the guide apparatus 10. The alignment block 42 can be selectively held relative to the rail portion 36 according to various embodiment, such as with a cam portion 140 defined by the enlarged knob 124.

The cam portion 140, illustrated particularly in FIGS. 3A and 3B, can be used to engage a tongue portion 142 of the rail portion 36. The handle 50 can be rotated around its longitudinal axis, generally in the direction of arrow G. Upon rotation of the handle 50, the cam 140 can be moved to engage the tongue portion 142 of the rail portion 36 and lock the alignment block 42 in a selected location. The handle 50 can also be rotated so that the cam portion 140 is drawn into the alignment block 42, as illustrated particularly in FIG. 3B, and allow free movement of the alignment block 42.

When the cam portion 140 extends from the alignment block 42 it can engage the tongue portion 142 to move the alignment block 42 away from the tongue portion 142. In moving the alignment block 42 away from the tongue portion 142, the extension fingers 44 can engage a top potion 144 of the rail portion 36 that defines the rail 48. When the extension portion 44 engages the top portion 144 of the rail 48, the alignment block 42 can be fixedly held relative to the rail portion 36. In this way, the third axis of movement of the alignment block 42 can be fixed or held immobile relative to the guide member 26.

In addition to the cam 140, which can be provided to substantially fix the alignment block 42 in a position relative to the rail portion 36, a plunger ball or spring loaded ball portion 148 can be provided in the alignment block 42. The plunger ball 148 can engage grooves 150 defined in the tongue portion 142. A spring member 152 can be provided in a bore 154 defined in the alignment block 42. The bore 154 can be a passage or any appropriate configuration to receive the spring member 152. The spring member 152 can bias the plunger ball 148 towards the grooves 150 defined in the tongue portion 142.

When moving the alignment block 42 along the rail 48, the plunger ball can move from groove to groove defined in the series or plurality of groves or detents 150. The grooves 150 can include a plurality of grooves that are positioned a selected distance from one another. For example, each of the grooves in the plurality of grooves 150 can be positioned about or substantially precisely one millimeter apart. Therefore, a positive indication of the movement of the alignment block 42 along the axis A can be provided by the physical feedback, such as auditory or touch. It will be understood that other feedback can be provided to a user, such as on a display device discussed further herein, but the plunger ball 148 can also be provided for feedback. It will be understood, that each of the other portions can include a similar feedback portion that can provide a selected indication of movement of the different portions relative to one another.

The movement of the alignment block 42 can be defined along the three axes A, B, and C. As briefly discussed above, the axis A, B, and C can be defined relative to the guide apparatus 10, according to various embodiments. Although the axis C is defined by a portion that is substantially immovable relative to the guide member 26, dynamic axes A and B can actually rotate around axis C. Therefore, although axes A and B are illustrated substantially fixed relative to ordinal coordinates of the guide member 26, it will be understood that each can rotate about axis C. For example, the first plate 30 can rotate about axis C so that axes A and B are actually moved relative to some defined point of the guide member 26. In other words, the bore 84 can define a fixed point in the guide member 26, therefore rotation of the first plate 30 will move axis A and B relative to the bore 84. Therefore, in one configuration the rail portion 36 can pivot about axis B that is substantially parallel to the two bores 84 and in a second position are positioned at an angle relative thereto.

It will be understood that the amount of rotation of axes A and B can be defined by the amount of rotation provided by the track portion 88. Similarly, the alignment block 42 can move along axis A that can be positioned at a selected angle relative to the bore 84 when the first plate 30 is moved. Therefore, one will understand, that the discussion herein of various axis or degrees of freedom defined by the guide apparatus can include discussion of axes positioned relative to the guide surface, which are not always fixed relative thereto.

Briefly, the three axes can relate to a selected bone portion, such as the femur 12. Thus, each of the axes can relate to a particular position or portion of resection. For example, one axis can be used to set or determine the amount of varus-valgus resection. Another axis can be used to set or determine the amount of flexion-extension resection. The final axis can be used to determine the amount of resection. One skilled in the art will understand that the particular axis used to define the particular anatomic feature will depend upon the orientation of the guided apparatus relative to the femur 12.

Each of the degrees of freedom relative to the axes can be individually and separately locked out relative to the other. The first lock out portion can be used when the other two are not being used, etc. Thus, the guide apparatus 10 can be used to determine and set each degree of freedom relative to the axes separately.

The tracking device, as discussed further herein, can be incorporated with the guide apparatus 10, such as in the slot 138 of the alignment block 42. Alternatively, the tracking device can be formed or integrated with the guide apparatus 10. Thus, the tracking device can be provided as a single piece with the guide apparatus 10 or as modular portion. Further, the tracking device can be any appropriate mode (e.g. electromagnetic, optical, fiber optic localization, etc.) as discussed herein. Incorporated tracking devices can have integrated wireless communication to the localization or tracking system. The guide apparatus 10 may also have servo or fiber optic motion detection components integrated that can either, via a wire or wirelessly, communicate the position of the device. For example, the fiber optic motion detection system can be incorporated into or positioned relative to the track 48 or the rail portion 36.

Figure 4:
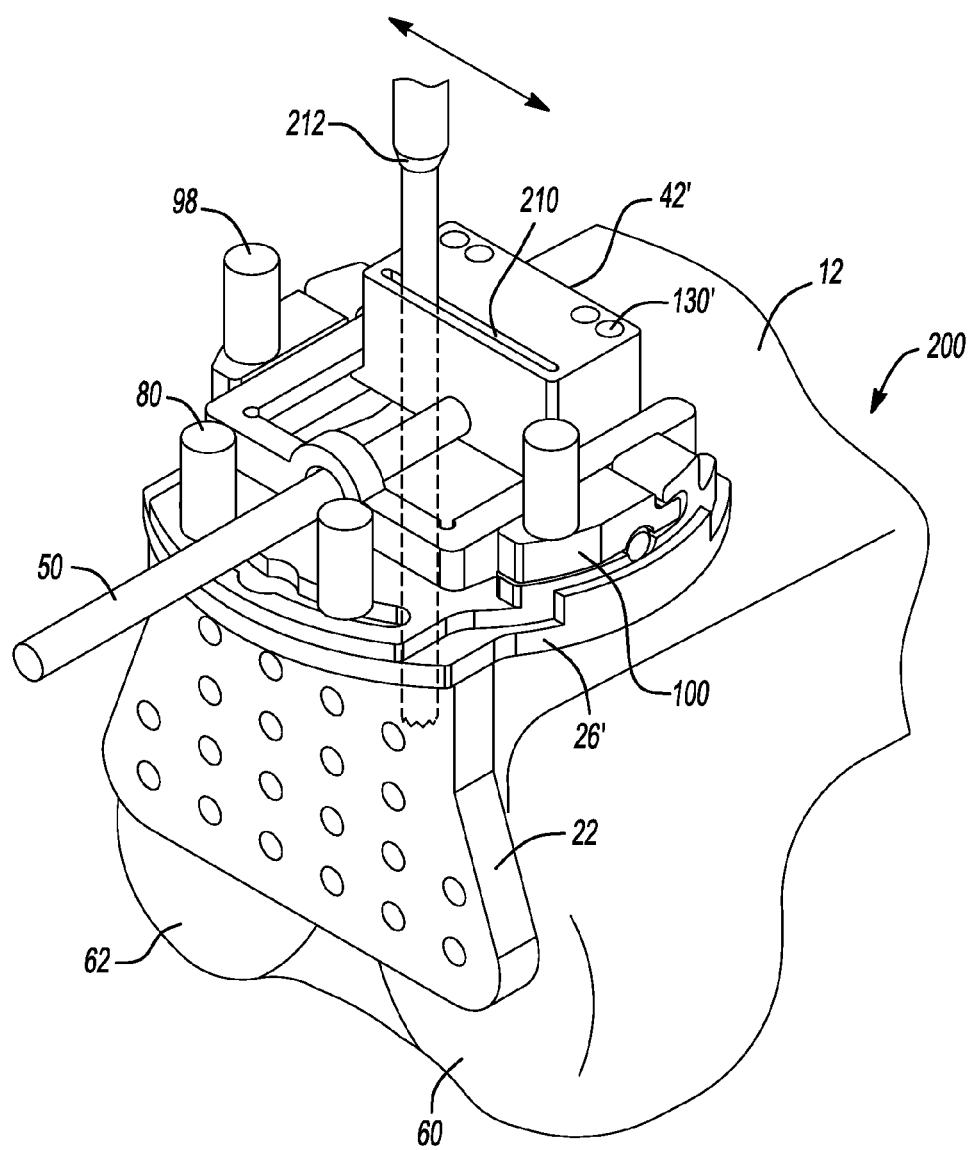
FIG. 4 is a perspective view of a guide apparatus according to various embodiments.
Figure 5:
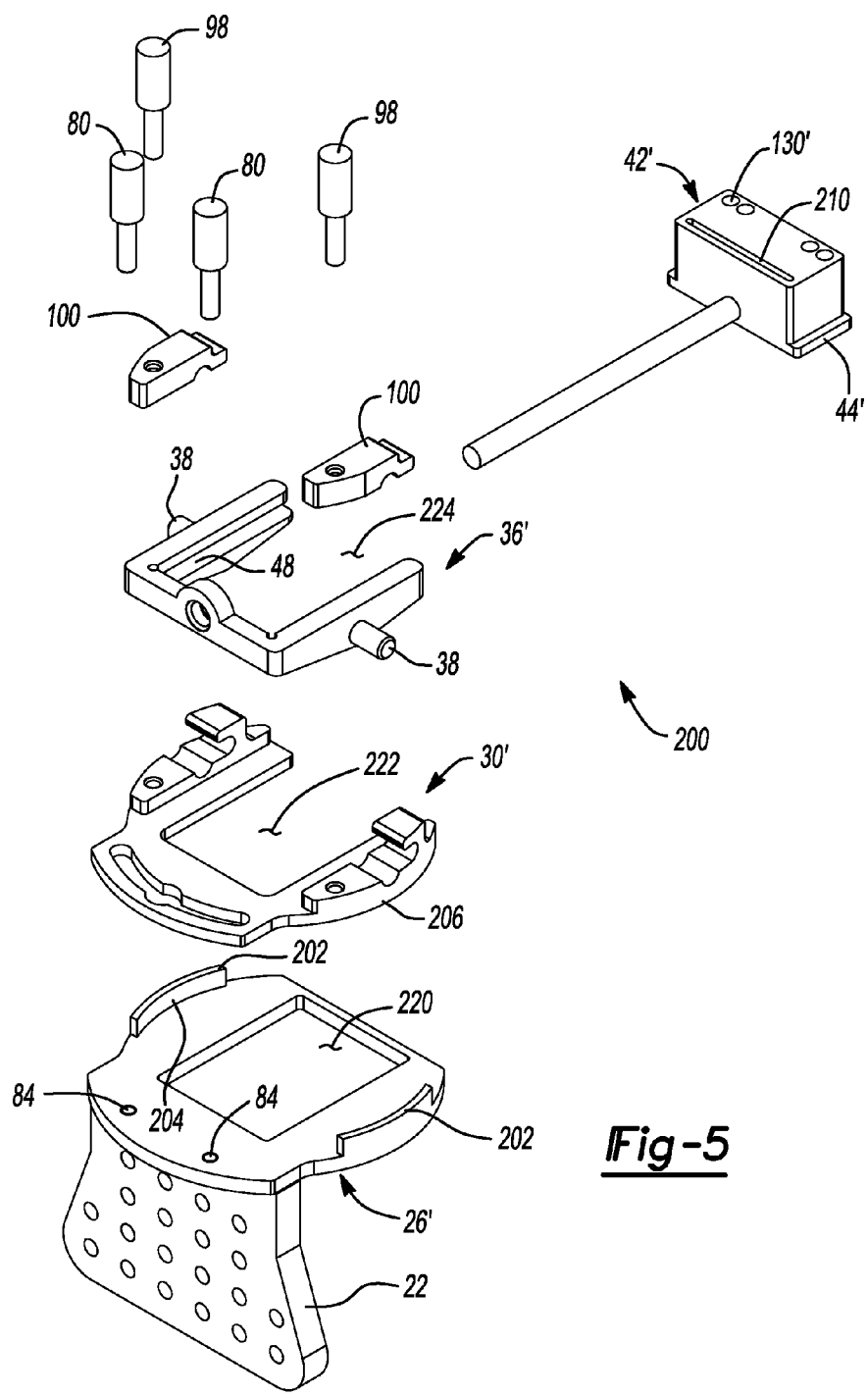
FIG. 5 is an exploded view of the guide apparatus of FIG. 4.

With reference to FIGS. 4 and 5, a guide apparatus 200, according to various embodiments, is illustrated. The guide apparatus 200 can include portions that are similar or substantially similar to the guide apparatus 10. Identical portions will be given identical reference numerals and substantially similar portions will be given reference numerals augmented with a prime. The guide apparatus 200 can include a bone contacting portion 22. Extending from the bone contacting portion can be the guiding member 26'. The guiding member 26' can be similar to the guiding member 26, save for various features. For example, the guiding member 26' can include a guiding portion track member 202. The track members 202 can define track surfaces 204 that cooperate with engagement or riding portions 206 defined by the first plate 30'.

The guide apparatus 200 can define axes that are substantially similar to the guide apparatus 10. Therefore, the guide apparatus 200 can define the three guide axes A, B, and C. The first plate 30' can rotate about axis C by having the track engagement members 206 engage the track members 202 on the guiding base 26'. The curvature of both the track members 202 and the track riding surfaces 206 can allow the first plate 30' to rotate about the axis C. The first set of locking screws 80 can still be provided to engage bores 84 and the guiding member 26' to lock the first plate 30' in a selected position relative to the guiding member 26'.

The rail portion 36' can also be substantially similar to the rail portion 36, such as including the pegs 38 and the rails 48. Further, a second set of locking screws 98 can cooperate with the locking members 100 to fix the rail portion 36' relative to the first plate 30'. Again, the pegs 38 can define the axis B about which the rail portion 36' can twist, rotate, or pivot.

Finally, the alignment block 42' can include track engagement members 44 that extend from the alignment block 42' to engage and ride within the rail 48. The alignment block 42' can define the guide holes 130' that are substantially similar to the guide bores 130 discussed above. Further, passages 130' can be orientated in any appropriate orientation on the alignment bock 42'.

The alignment block 42' can also define a guide slot 210. The guide slot 210 can cooperate with a tracking device, in a manner substantially identical to the passage 138 of the alignment block 42. Alternatively, or in addition thereto, the guide slot 210 can define a resection guide surface. The guide slot 210 can be substantially elongated to guide a saw, or having a selected width to guide a drill, or any appropriate device.

According to various embodiments, the guide slot 210 can be provided to guide a saw 212. The saw 212 can resect a portion of the femur 12, or any appropriate portion of the anatomy. If the alignment block 42' is positioned near or on an anterior portion of the femur, the saw 212 can be used to resect a distal end of the femur 12. It will be understood that the alignment block 42' can be positioned relative to any appropriate bone portion and can be used to resect any appropriate portion of bone. Nevertheless, the guide assembly 200 can include portions to allow the saw blade 212 to be guided directly with the alignment block 42'.

Each of the axes defining or movement members can include a passage. For example, the guide member 26' can include a first passage 220, the first plate 30' can include a second passage 222, and the rail portion 36' can include a third passage 224. Each of the passages 220, 222, 224 can allow a substantially free or open access to the bone portion to which the alignment or guide apparatus 200 is interconnected. Therefore, according to various embodiments, the saw blade 212 can be guided directly with the alignment block 42' to resect a selected portion of the anatomy, such as a distal portion 14 of the femur.

Figure 6:
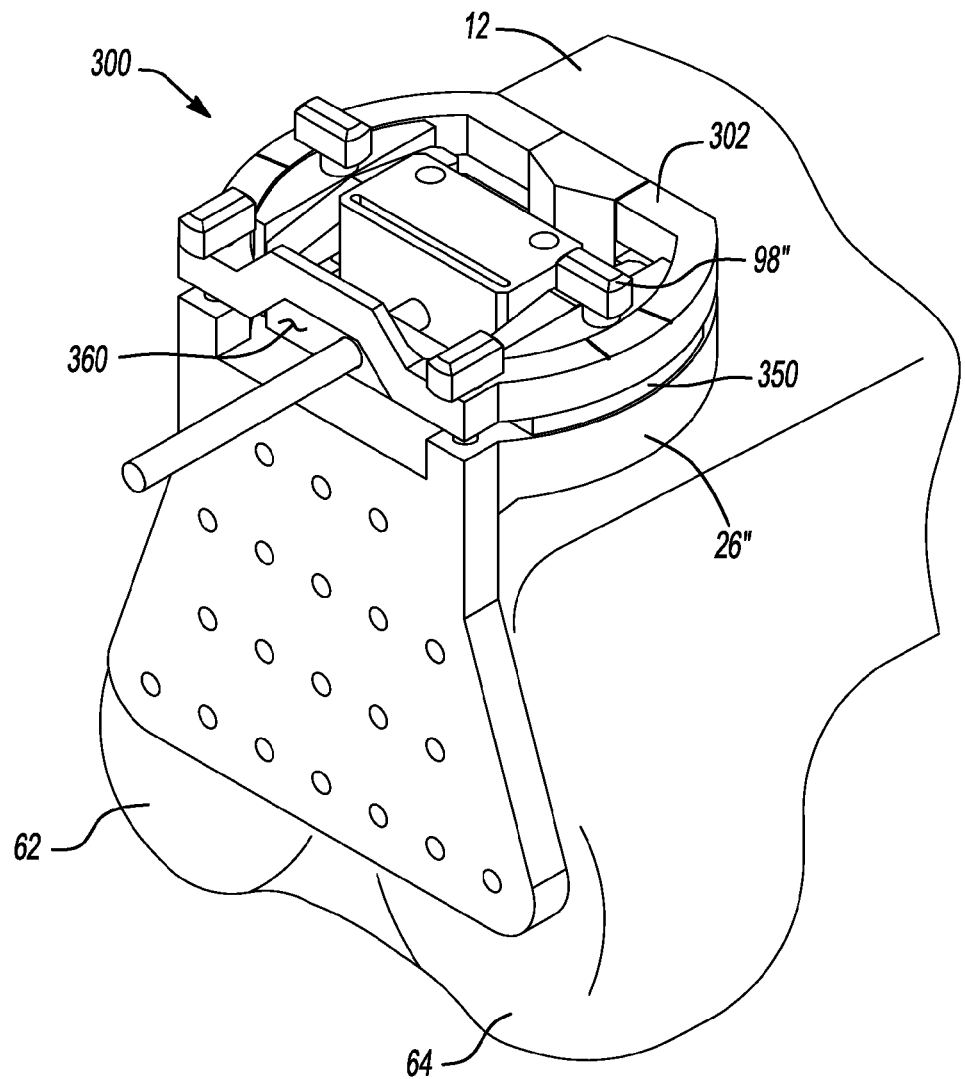
FIG. 6 is a perspective view of a guide apparatus according to various embodiments.
Figure 7:
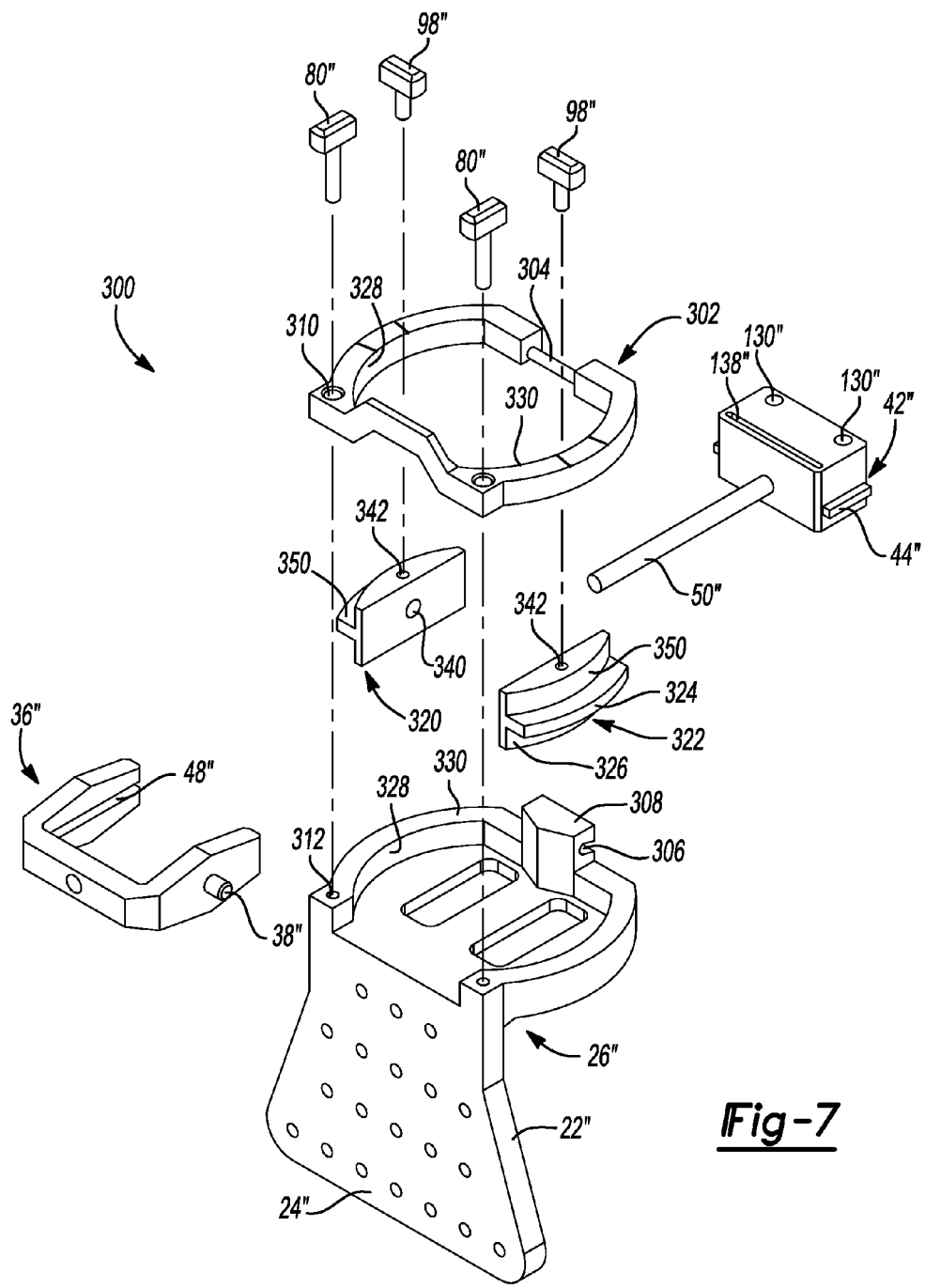
FIG. 7 is an exploded view of the guide apparatus of FIG. 6.

With reference to FIGS. 6 and 7, a guide apparatus 300 is illustrated. The guide apparatus can include portions that are similar or substantially similar to the guide apparatuses discussed above. It will be understood that portions that are substantially identical to portions described above will be indicated with identical reference numerals. Portions that are slightly altered will be referenced with reference numerals that are identical but include a double prime. The guide apparatus 300 can be used to guide an alignment block 42" relative to the femur 12, or any other appropriate portion of the anatomy. The guide apparatus 300 can also include a bone contact portion 22".

The guide apparatus 300 can include a guide surface top plate or clamping plate 302. The top plate 302 can extend around a perimeter that is substantially similarly to the perimeter of the guide plate 26". The top plate 302 can include a pin or reduced size portion 304 that extends around the portion of the perimeter of the top plate 302. The reduced size portion 304 can cooperate with a slot 306 defined by a projection 308 from the guide plate 26". This can allow the top plate 302 to hinge or move relative to the guide plate 26". The top plate 302 can also define a bore or passage 310 that can allow a first locking portion 80" to extend through. The guiding plate 26" can also define a bore or passage 312 that can cooperate with the first locking portion 80".

Two portions 320 and 322 can be provided that include exterior surfaces 324 and 326 that can articulate or move along respective surfaces 328 and 330 of the guiding plate 26" and the top plate 302. The articulating exterior surfaces 328, 330 can cooperate with the surfaces 324, 326 of the two portions 320, 322 to allow the two portions to rotate about the axis C of the guide apparatus 300. The two portions 320, 322 can be interconnected with the rail portion 36" via pegs or arms 38" that can extend into a passage or bore 340 defined in the two portions 320, 322. Second locking portions 98" can extend through bores 342 defined in the portions 320, 322 to urge against the pegs 38".

When assembled, as illustrated in FIG. 6, projections 350 from the portion 320, 322 can extend between the top plate 302 and the guiding surface or plates 26". The first locking portions 80" can pass through the passages 310 and 312 and be used to apply a force between the top plate 302 and the guiding plate 26" to compress against the projections 350 to hold the portions 320, 322 in a selected position. Similarly, the second locking portions 98" can cooperate with the bores 342 to compress against the pegs 38" to hold the rail portion 36" in a selected orientation. The alignment guide 42" can include projections 44" similar to the projections discussed above that can ride on the rails 48" defined by the rail portion 36". Similarly a handle 50" can be provided to move the alignment member 42" relative to each of the three axes defined by the guide apparatus 300. In addition, the top plate 302 can include a recess or opening portion 360 to allow the handle 50" to move relative to the guide apparatus 300.

The guide block 42" can include a slot 138" and alignment bores or passages 130". These portions can be similar to the portions described above to allow for the passage of alignment pins 132 or positioning of tracking devices.

Figure 8:
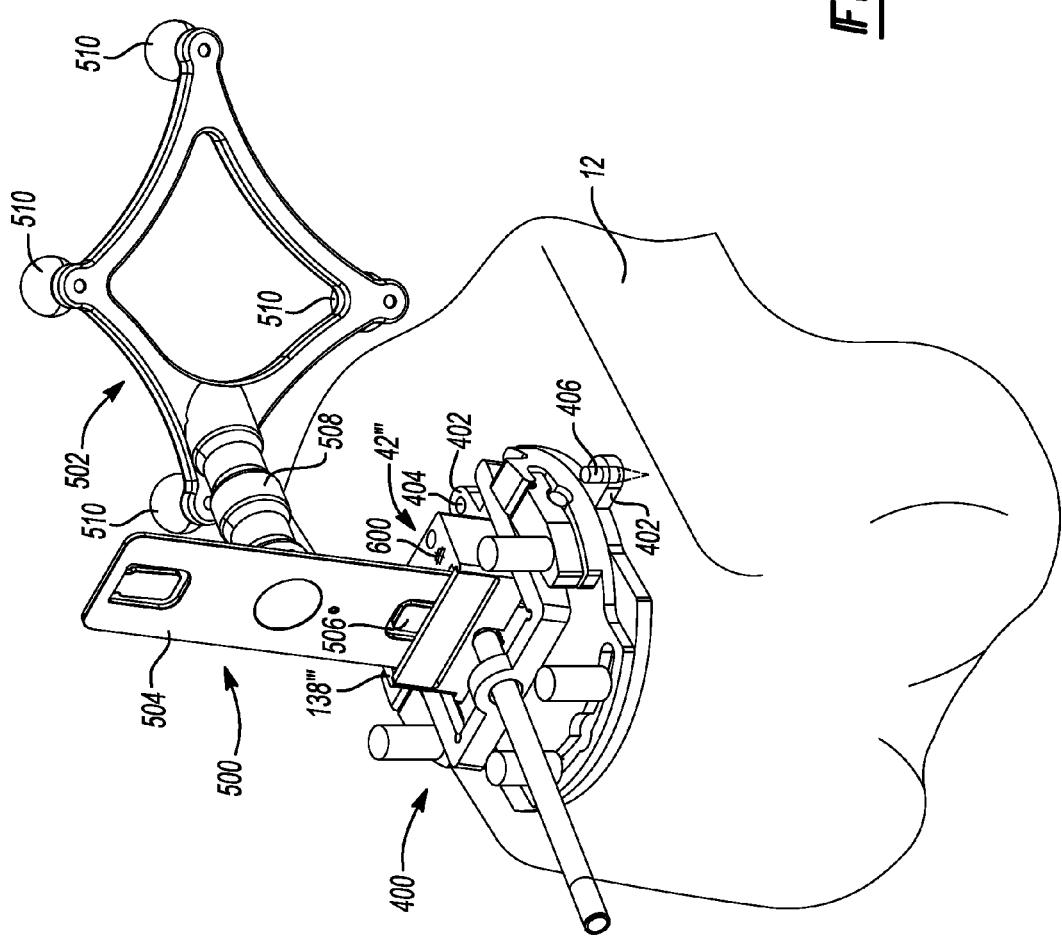
FIG. 8 is a perspective view of a guide apparatus according to various embodiments.

With reference to FIG. 8, a guide apparatus 400, according to various embodiments, is illustrated. The guide apparatus 400 can be substantially similar to the guide apparatus 10, illustrated and discussed in relationship to FIGS. 1-3b. Therefore, the details of the guide apparatus 400 are substantially described above and will not be repeated here. The guide apparatus 400, however, can differ from the guide apparatus 10, according to various embodiments, in that it is does not include the bone contacting portion 22. Although the guide apparatus 400 can operate in a manner substantially identical to the guide apparatus 10 discussed above, the guide apparatus 400 can be affixed to the femur 12 via bone fixation projections 402. The projections 402 can define a bore 404 through which a fixation pin 406 can be positioned. The fixation pin 406 can be passed into the femur 12, or any appropriate bone portion, to interconnect the guide apparatus 400 with the femur 12. The alignment block 42''' can then be moved relative to the femur 12, as discussed above.

Also, a tracking device 500 can be interconnected with the slot 138'''. The tracking device can be used with a surgical navigation system 600, illustrated in FIG. 11, to determine or navigate a position of the alignment block, according to various embodiments. The tracking device 500 can be provided in any appropriate manner. Also, the tracking device 500 can include any appropriate track-able portion, such as an optical tracking portion 502. The optical tracking portion 502 can be connected to an alignment guide connection portion 504. The alignment guide connection portion 504 can include a locking portion, such as a spring locking portion 506. The spring locking portion 506 can cooperate or interact with the slot 138''' to hold the tracking device 500 relative to the alignment block 42'''. Further, it will be understood that the alignment guide connection portion 504 can be interconnected with any alignment guide according to various embodiments. It will also be understood, that the tracking device 500 can be interconnected with an alignment block according to various embodiments.

The optical tracking portion can extend from a stem or holder arm 508 and include an optical tracking portion 510 or plurality of optical tracking portions 510. The optical tracking portions 510 can be active or passive. For example, an active optical tracking portion can include a LED or powered tracking portion. Alternatively, or in addition thereto, the optical tracking portions 510 can include passive optical tracking portions that can be balls or members that reflect a selected wave length of light energy.

In addition to the optical tracking device 500, or alternatively thereto, any other appropriate tracking device can be provided. For example, acoustic, radar, accelerometer, or electromagnetic tracking devices can be provided.

According to various embodiments, an electromagnetic tracking device 600 can be interconnected with the alignment guide 42'''. The electromagnetic tracking device 600 can be embedded within the alignment portion 42''', such as within a bore or hollow portion formed therein. The bore or hollow portion can be covered with a selected epoxy to allow the tracking device 600 to interact with an electromagnetic tracking system. In addition, the electromagnetic tracking device can be provided in a size that can sit substantially proud of the alignment block 42''', without substantially interfering with the working thereof.

The guide apparatus, according to various embodiments, can be formed of selected materials. For example, when electromagnetic tracking device 600 is interconnected with the alignment block 42''', or the guide block according to various embodiments, the alignment block may be selectively formed of a polymer or non-magnetic or metallic material. For example, the alignment guide 42''' can be formed of a substantially rigid or hard polymer to allow the tracking device 600 to be used without interference in an electromagnetic tracking system. The other portions of the guiding apparatus can be provided of metal or other portions that would not interfere with the electromagnetic tracking system. Further, it will be understood, that the entire tracking apparatus can be provided of polymer or non-metallic materials. Specific examples include, alloys of cobalt chromium, titanium, stainless steel alloys, carbon fiber, and ceramic materials. Similarly, the tracking device, or various portions thereof, can be provided in a substantially multiple use or single use material or configuration. Each portion the guide apparatus, according to the various embodiments, can be formed of selected materials.

Further, according to various embodiments, each portion of the guiding apparatus can be provided with a tracking device, such as the tracking device 600. Therefore, rather than only tracking the position of the alignment block 42''', each portion of the guide apparatus can be tracked.

Figure 9:
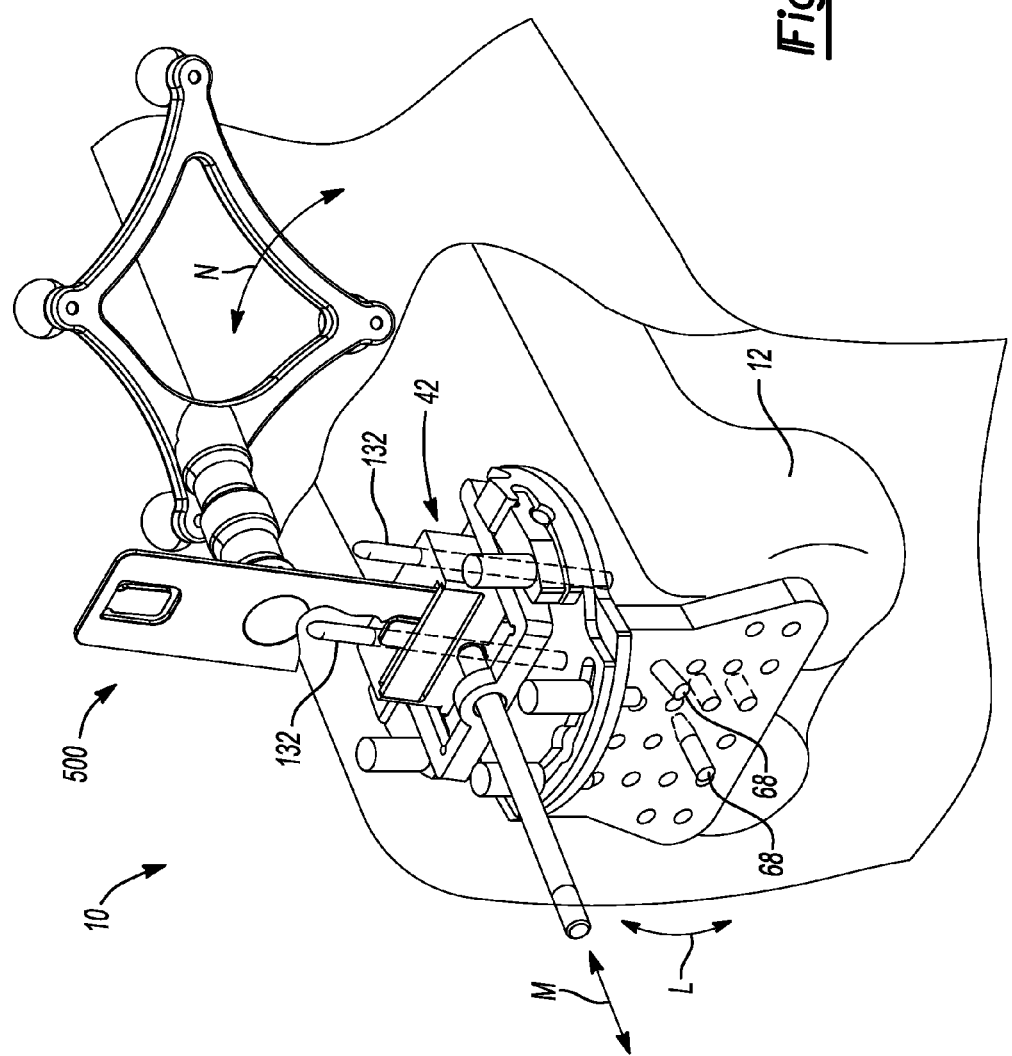
FIG. 9 is an environmental view of a tracking device associated with a guide apparatus according to various embodiments.
Figure 10:
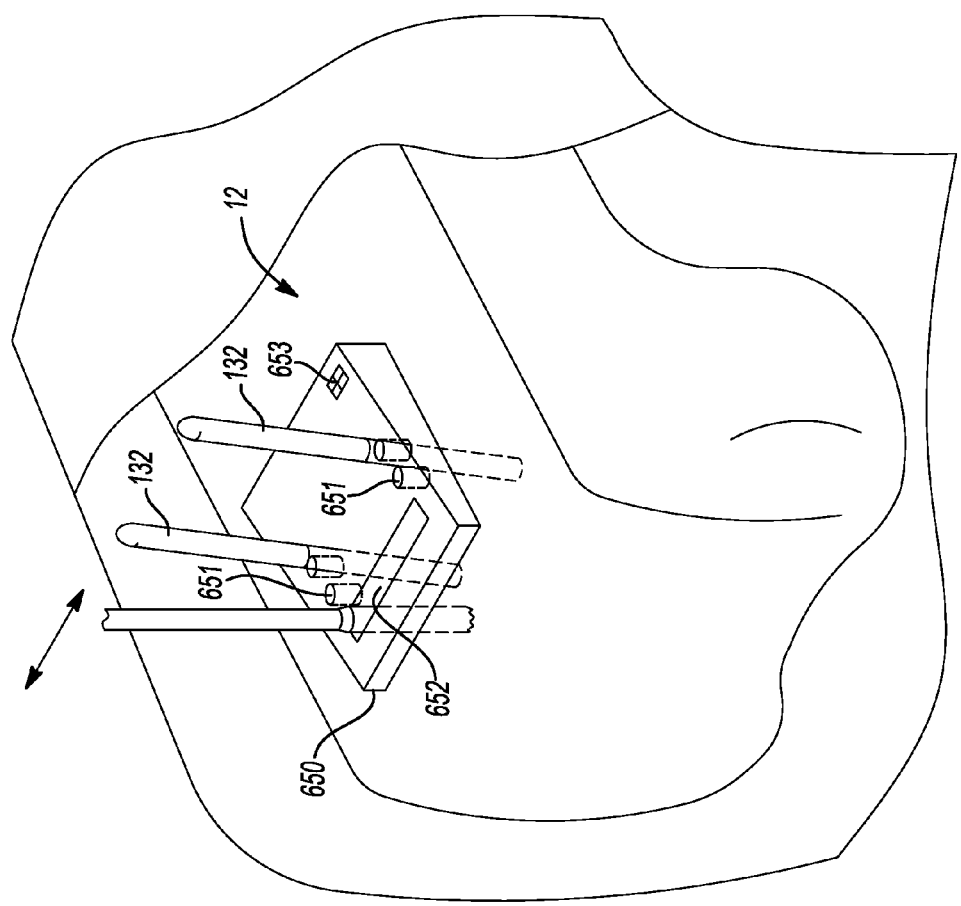
FIG. 10 is an environmental view of a guide block guiding a saw during a resection and mounted on pins positioned with a guide apparatus.

With reference to FIGS. 9 and 10, according to various embodiments, the guide apparatus 10 can be used to position one or more of the alignment pins 132 relative to a bone, such as the femur 12. As discussed above, the alignment block 42 can be moved relative to the three axes A, B, and C defined by the guide apparatus 10. The axes allow the alignment block 42 to move in three degrees of freedom.

Initially, the guide apparatus 10, according to various embodiments, can be positioned relative to a bone, such as the femur with the bone contacting portion. As discussed above, the fixation pins 68 can be used to fix the guide apparatus to the bone. The pins can be selectively positioned in the bone contacting portion positioned in an initial or gross alignment portion. Thus, the bone contacting portion, the passages 24 there through, and the fixation pins 68 can be used in a first instance to align the alignment block 42 relative to the bone 12.

As discussed above, the bone contacting portion 22 can be used to connect the guide apparatus 10 to the bone. The bone contacting portion 22 can also be provided in a modular manner. The bone contacting portion 22 can be interconnected with the guide portion 26. Also, each of a plurality of the bone contacting portions 22 can include a different configuration of the passages 24. As discussed above, the bone contacting portion 22 can include a selected configuration for the initial or gross connection.

The alignment guide 42 can move in a sliding direction M along axis A on the rail portion or axis defining portion, according to various embodiments. As discussed above, axis A can be moved due to rotation of the alignment guide 42 around axis C. Axis C allows the alignment guide 42 to rotate in direction N, generally via the first plate or axis defining portion. The direction N can be around the alignment bore 130 defined by the alignment guide 42. Finally, the guide apparatus 10 allows the alignment guide 42 to rotate around axis B in direction L, generally by the interaction of the rail portion or axis defining member and the first plate. The rotation around the axis B, defined by the arrow L, can also be moved relative to the guide apparatus 10, such as the guiding plate 26, due to rotation of the alignment guide 42 around axis C.

As illustrated here and above, the movement of the guide apparatus 10, and particularly the alignment block 42 can be efficient. The movement of the alignment block around or relative to one axis does not or only minimally affects the location of the other axis. Simply put, the axes A, B, and C of the guide apparatus 10 are generally coincident with one another. For example, moving the alignment block around axis B does not or only minimally moves the alignment block relative to axis A.

Also, movement and adjustment mechanism of the guide apparatus 10 is substantially contained within the boundaries of the device. That is the origin or common point of all of the axes A, B, and C can be within the outer bounds of the guide apparatus 10. There are, generally, no components of the guide apparatus, according to various embodiments that extend far from a boundary of the apparatus.

The position of the alignment guide 42, and by correlation the position of the passages 130, can be determined with the tracking device 500, which can be used in the navigation system, as discussed further herein. The navigation system can track the position of the alignment guide 42 relative to the anatomy. Thus, the position of the passages 130 relative to the femur 12 can be determined.

The alignment guide 42 can be moved by a user until a selected orientation is achieved relative to the femur 12. The orientation of the alignment guide 42 relative to the femur can be based upon the three degrees of freedom. Further, the orientation can be predetermined, such as prior to a procedure. Alternatively, the appropriate position can be determined, intra-operatively and can be based upon various data regarding the patient.

Once the appropriate orientation of the alignment member 42 is determined, the various locking portions can be engaged. According to various embodiments the locking portions can include thumb screws, finger screws, etc. with knurled ends for manual manipulation. It will be understood, however, that tools can be used to tighten or engage the locking portions. Even the handle 50 can be manually moved to lock the alignment guide 42 or can be operated with a tool to lock the member in place.

In addition, as discussed above, the various locking portions can be operated individually and separately. Thus, the first locking portion can be used to lock the apparatus relative to axis C. The second locking portion can be used to lock the apparatus in relation to axis B. The final or third locking portion can lock the apparatus relative to axis A. It will be understood, however, that the various locking portions can be engaged separately and at any selected time.

A user can selected to engage the first locking portion and not the others. In this way, the separate axes can be separately used. For example, a resection depth could be selected by movement of the alignment block, according to various embodiments, and the respective axis and locking portion fixed relative to the anatomy. In this situation, the alignment block could still be moved relative to the other two axes.

Once the apparatus, according to various embodiments is locked in position, the alignment pins 132 or reference holes can be positioned into the femur 12 through the passages 130. It will be understood, however, that the guide apparatus 10, according to various embodiments, need not be locked to position the pins 132. Positioning the alignment pins 132 into the femur 12 can allow the interconnection of a cutting block 650 with the alignment pins 132, illustrated in FIG. 10. Also, reference bores can be formed through the alignment block and the pins can be placed after the apparatus 10 is removed. The cutting block 650 can define a guide slot 652 to guide a saw blade, such as the saw blade 212. The saw blade 212 can be any appropriate saw blade and driven by any appropriate motor, such as a reciprocating or oscillating saw blade.

The alignment member 42 can also include a modular or removable member that defines the passages 130. The interchangeable plates can be provided for varying or different cutting guides 650. The interchangeable plates can be specific or designed for specific or selected configurations of the cutting guide 650. For example, the cutting guide 650 can include two fixation bores at two corners and a plate can include the same configuration. Also, a plurality of alignment guides can be included for selection by a user 721. Each of the alignment guides can be provided in a kit and can include a different passage 130 configuration, similar to the plates. Thus, a user can select a plate to position on the alignment member 42 or one of a plurality of alignment guide 42 to match the cutting guide 650 selected to be used. The plates can be interconnected with the alignment guide 42 in any appropriate manner, such as a tongue an groove, dovetail, snap fit, etc.

The guide apparatus 10 can be removed, such as by removing the mounting pins 68 from the femur 12 and removing the guide apparatus 10 from the femur 12. The guide apparatus 10 can also be removed according to various embodiments, such as sliding the guide apparatus off the fixation pins 68. The alignment pins 132 can remain in place to provide a reference for the cutting block 650. Alternatively, the passages 130 can be used to form holes in the femur 12 and only those are left in place and the alignment pins 132 are attached after the guide apparatus 10 is removed. The alignment pins 132 can also be used to fix the cutting block 650 to the femur 12. In this way, the femur 12 can be resected a selected amount.

The guide apparatus can also include a portion that remains affixed to the bone. The portion that remains affixed can be a modular piece from the remaining portion of the guide apparatus 10. For example, the bone fixation member 22, one of the bone attachment portions 402, or any appropriate portion. The portion that remains can include a tracking device or include the tracking device 500, 600. The remaining portion can then be tracked for cut validation, dynamic referencing, or for other appropriate purposes.

The cutting guide 650 can also include a plurality of bores 651 to receive or pass over the alignment pins 132. The plurality of bores 651 can be used to reposition or fine tune the position of the cutting guide 650. Also, the various bores 651 can be used for a second or refinement cut after trialing a prosthesis member.

In addition, a tracking device 653 can be included or associated with the cutting guide 650. The tracking device can be modular or formed integrally with the cutting guide 650. The tracking device 653 can be used to track the location of the cutting guide 650 or portions thereof. Thus, as discussed herein, the positions of the cutting guide or the guiding portions thereof (e.g. slots or edges) can be tracked and illustrated on a display device.

Figure 11:
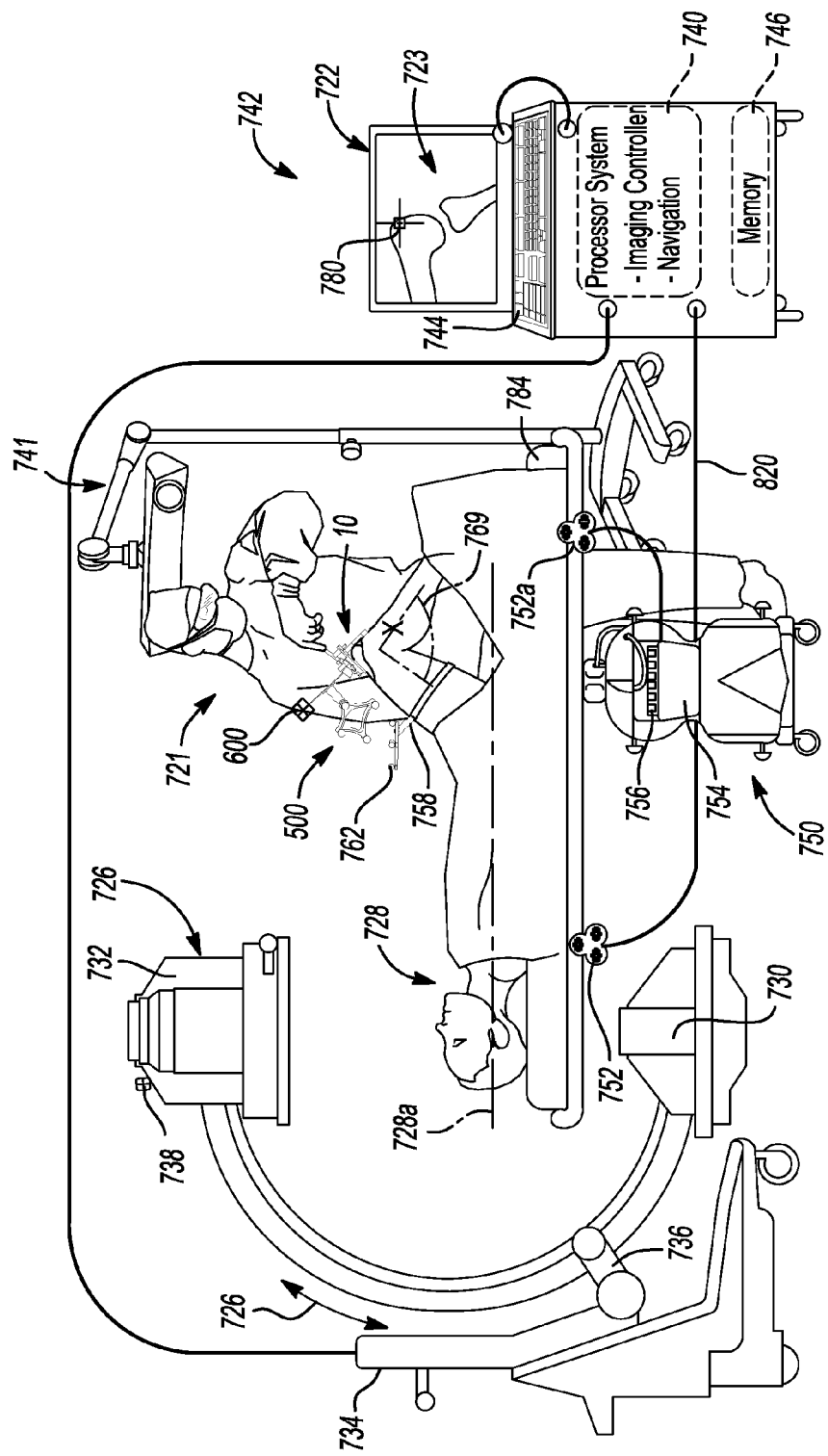
FIG. 11 is an environmental view of a guide apparatus, according to various embodiments.

With reference to FIG. 11, a surgical navigation system 700 is illustrated. The navigation system 700 can allow a user, such as a surgeon 721 to view on a display device 722, a relative position of an instrument, such as the guide apparatus 10, to a coordinate system. It will be understood that the navigation system can also be used to determine a position of the guide apparatus, such as the alignment block 42.

The coordinate system can be relative to image data displayed on the display device 722, to a patient only, to a point outside of a patient, or combinations of these. Further, the navigation system 700 can be used with image data, imageless or without image data, atlas data specific image data, or combinations of these. For example, a graph or line model of the respective portions can be illustrated in the display device 722. As discussed above a plane or line can be determined by tracking the bone contacting portion 22 as can lines representing the position of the alignment block 42, etc.

In an imageless system or application, representations of the anatomy can be displayed on the display device 722 as opposed to acquired image data of the patient 728 (e.g. MRI scans, CT scans, etc.). The imageless data can include a combination of kinematics and a plurality of anatomical points, creating a mathematical representation of the individual anatomy, allowing the measurement of angles and distances between navigated devices and the computed anatomical representation. The anatomical points can include points that are determined with the guide apparatus 10, according to various embodiments. As discussed above, the bone contacting portion 22 can contact points on the femur 12 that define a plane and that plane can be displayed on the display device via tracking the tracking device 500, 600. The points on the anatomy can be spatial or anatomical landmarks that are representative of the anatomy for display on the display device 722.

The representations of the anatomy can include lines and angles on the display device 722. The lines and angles can be used to guide the guide apparatus and other instruments relative to the patient 728. The representations can be used in place or in addition to image data of the patient for the navigation. It will also be understood that the representations can be registered to the patient 728. Alternatively, the representations on the display device 722 can created due to direct contact or tracking of a portion of the anatomy. Thus, registration to "preacquired" images may not be necessary.

It should further be noted that the navigation system 700 can be used to navigate or track various instruments including: cannulas, catheters, probes, needles, guidewires, instruments, implants, deep brain stimulators, electrical leads, guide apparatuses, etc. Moreover, the guide apparatus 10 can be used in any region of the body. The navigation system 700 and the guide apparatus 10 can be used in any appropriate procedure, such as one that is generally minimally invasive, arthroscopic, percutaneous, stereotactic, or an open procedure.

Also, the illustrated guide apparatus 10 is only exemplary of any appropriate instrument and may also represent many instruments, such as a series or group of instruments. Identity and other information relating to the guide apparatus 10 can also be provided to the navigation system 700. Further, the information about the guide apparatus 10 can also be displayed on the display device 722 for viewing by the surgeon 721.

The navigation system 700 can include an imaging device 726 that is used to acquire pre-, intra-, or post-operative or real-time image data of a patient 728. The imaging device 726 can be, for example, a fluoroscopic x-ray imaging device that may be configured as, and also referred to as, a C-arm 726 having an x-ray source 730 and an x-ray receiving section 732. The sections can be mounted relative to one another and moveable relative to a base 735. The base 735 can be fixed relative to the patient 728. An optional calibration and tracking target and optional radiation sensors can be provided, as understood by one skilled in the art. An example of a fluoroscopic C-arm x-ray device that may be used as the imaging device 726 is the ARCADIS® Orbic or ARCADIS® Orbic 3D from Siemens Medical of Germany. Other exemplary fluoroscopes include bi-plane fluoroscopic systems, ceiling fluoroscopic systems, cath-lab fluoroscopic systems, fixed C-arm fluoroscopic systems, 3D fluoroscopic systems, O-arm™ imaging devices (i.e. devices sold by Breakaway Imaging, LLC. having a place of business in Massachusetts, USA), etc.

An optional imaging device controller 734 can control the imaging device 726 to capture the x-ray images received at the receiving section 732 and store the images for later use. The receiving section 732 can also be referred to as or act as, according to various embodiments, an image collection section or image intensifier. The controller 734 may also be separate from the C-arm 726 or located a distance from the C-arm 726. The controller 734 can control the C-arm 726 to control movement in the direction of arrow 726a or rotate about a longitudinal axis 728a of the patient 728, allowing anterior or lateral views of the patient 728 to be imaged. Each of these movements involves rotation about a mechanical axis 736 of the C-arm 726.

The operation of the C-arm 726 is understood by one skilled in the art and not repeated in detail here. Briefly, however, x-rays can be emitted from an x-ray section 730 and received at a receiving section 732. The receiving section 732 can include a camera that can create the image data from the received x-rays. Further, a C-arm tracking device 738 can be provided to track a position of any portion of the C-arm 726, such as the receiving section 732, at any appropriate time by a tracking system 750.

It will be understood that image data can be created or captured with any appropriate imaging device, such as a magnetic resonance imaging system, a positron emission tomography system, computed tomography, or any appropriate system. It will be further understood that various imaging systems can be calibrated according to various known techniques. The use of the C-arm 726, however, can be used according to various embodiments disclosed herein.

The image data can be forwarded from the C-arm controller 734 to a navigation computer and/or processor system 740 via a communication system 741. The communication system 741 can be wireless, wired, a data transfer device (e.g. a CD-Rom or DVD-Rom), or any appropriate system. The processor system 740 can also include the C-arm controller 734. The C-arm controller 734 and the processor system 740 can also, therefore, include a BUS communication system or internal communication. It will also be understood that the image data is not necessarily first retained in the controller 734, but may be directly transmitted to a workstation 742 or to the tracking system 750, as discussed herein.

A work station 742 can include the processor system 740, the display device 722, a user interface 744, and a memory 746. The processor system 740 can process the image data, navigation data, planning data, treatment area data, etc. The processor system 740 can include one or multiple separate processors to execute selected instructions or perform various tasks.

The work station 742 provides facilities for displaying the image data 723 as an image on the display device 722, saving, digitally manipulating, or printing a hard copy image of the received image data 723. The user interface 744 may be a keyboard, mouse, touch pen, touch screen or other suitable device. The user interface device 744 allows a physician or user to provide inputs to control the imaging device 726, via the C-arm controller 734, or adjust the display settings of the display device 722. The user interface 744 can also allow a user to manipulate the navigation system 700 in any selected manner.

While the imaging device 726 is shown in FIG. 11 as a C-arm, any other alternative 2D, 3D or 4D imaging modality may also be used. As disclosed herein any appropriate imaging system can be used in the navigation system to provide image data. The imaging system 726 can generally provide information regarding movement of a capturing or receiving section 732 thereof to determine a position of the capturing portion relative to the patient 728. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 728. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion of optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 728. It should further be noted that the optional imaging device 726, as shown in FIG. 11, provides a virtual bi-plane image using a single-head C-arm fluoroscope as the optional imaging device 726 by simply rotating the C-arm 726 about at least two planes, which could be orthogonal planes to generate two-dimensional images that can be converted to three-dimensional volumetric images. By acquiring images in more than one plane, an icon representing the location of a guide apparatus, an impactor, stylet, reamer driver, taps, drill, deep brain stimulators, electrical leads, needles, implants, probes, or other instrument, introduced and advanced in the patient 728, may be superimposed in more than one view on the display device 722. Displaying an icon in multiple views can allow simulated bi-plane or even multi-plane views, including two and three-dimensional views.

With continuing reference to FIG. 11, the navigation system 700 can further include the tracking system, such as an electromagnetic (EM) tracking system 750 that includes a localizer 752 (e.g. a coil array or multiple coil arrays), a coil array controller 754, a navigation interface 756 for an instrument tracking device, and a dynamic reference frame 758. The dynamic reference frame 758 can be used to determine at any point in time a position of the patient 728 in the navigated space. One skilled in the art will understand, however, that any appropriate navigation system can be used, such as an optical navigation system, a radar navigation system, an acoustic navigation system, etc.

The dynamic reference frame 758 can include a dynamic reference frame member or holder 760 and a removable tracking device 762. Alternatively, the dynamic reference frame 758 can include a tracking device that is formed integrally with the dynamic reference frame member 760. One skilled in the art will understand that the tracking device 762 can be any appropriate device that can be an emitter, a receiver, a reflector, a sensor to sense a field, or any other appropriate device that can be tracked by a tracking system including the localizer 752.

The localizer coil array 752 may also be supplemented or replaced with a second localizer 752a. The second localizer 752a may be the same as the first localizer 752 or different, such as that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference.

As is understood, the localizer array 752 can transmit signals that are received by an appropriate tracking device. The signal transmitted by the localizer 752 can be an electromagnetic field that will have a different strength at any position in the field. The coil array 752 can include a plurality of coils each operable to generate distinct electromagnetic fields into the navigation region of the patient 728, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The tracking device, such as the tracking device 762 of the dynamic reference frame 758, the instrument tracking device 600 on the guide apparatus 10, the tracking device 738 on the imaging device 726, etc. can sense the field strength at their respective locations. The tracking device 762 of the dynamic reference frame 758, the instrument tracking device 600, and the tracking device 738 can then transmit signals based upon the received signals from the array 752, 752a. One skilled in the art will also understand that the localizer 752, 752a can receive or sense a field produced by the various tracking devices 762, 600, and 738. Thus, the system can work in either manner or a combination.

It should further be noted that the entire tracking system 750 or parts of the tracking system 750 may be incorporated into the imaging device 726. For example, one of the localizers can be incorporated into the imaging device 726. Incorporating the tracking system 750 may provide an integrated imaging and tracking system. Any combination of these components may also be incorporated into the imaging system 726, which can include any appropriate imaging device.

The coil array 752, which can include multiple individual coils, can be positioned at any appropriate location. For example it can be attached to the receiving section 732 of the C-arm 726. Alternatively, the coil array 752 may be positioned at the x-ray source 730, within or atop an operating room (OR) table 784, on side rails associated with the OR table 784, or positioned on the patient 728. The coil array 752 may also be positioned in the items being navigated.

The coil array 752 is controlled or driven by the coil array controller 754. The coil array controller 754 can drive each coil in the coil array 752 in a time division multiplex or a frequency division multiplex manner. In this regard, each coil may be driven separately at a distinct time or all of the coils may be driven simultaneously with each being driven at a different frequency, as discussed further herein. This arrangement makes the coil array 752 a transmitter coil array. It will be understood that the coil array may also receive, as discussed above. Thus, reference to a transmitter coil array is merely exemplary and not intended to limit the type of localizer used in a selected tracking system.

Upon driving the coils in the transmitter coil array 752 with the coil array controller 754, electromagnetic fields are generated within the patient 728, which is sometimes referred to as patient space. The electromagnetic fields generated in the patient space induce currents to produce signals in the tracking devices 600, 738, 762 positioned in the navigation field. These induced signals are delivered to the navigation device interface 756 and can be forwarded to the coil array controller 754, as discussed above. Again, it will be understood that the tracking devices may transmit a field and induce a signal in the localizer 752.

The navigation device interface 754 may provide all the necessary electrical isolation for the navigation system 700, as discussed herein. The navigation device interface 756 can also include amplifiers, filters and buffers to directly interface with the tracking devices 600, 738, 762. Alternatively, the tracking devices 600, 738, 762 or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical transmission line to the navigation device interface 756. For example, batteries and LC tank circuits can be provided to power the various tracking devices. These powered portions can be used to power wireless communication portions, such as communication of a tracking device in a tracking system.

When the navigation system 700 uses an EM based tracking system, various portions of the navigation system 700 are equipped with at least one coil and generally multiple coils. The coils can be used with the EM localizer arrays 752, 752a to determine a position of the coils. The coils are generally defined by tracking devices 600, 738, 762 that are associated with the portions to be tracked. Thus, determining a position of the coils allows a determination of a position of the tracking devices and the portions to which they are attached. Alternatively, the tracking system 750 may be a hybrid system that includes components from various tracking systems such as optical, acoustic, radiation, radar, etc.

The tracking device 600 on the guide apparatus 10 can be associated with a base that is attached to a selected portion of the guide apparatus. For example, the tracking device 600 can be interconnected with the base 504 (FIG. 8). Alternatively, the tracking device 600 can be incorporated or imbedded in a portion of the guide apparatus 10. As a further alternative, the tracking device can include an optically tracked portion, such as the tracking device 500. This can also be interconnected via the base 504 with the guide apparatus 10.

An alternative tracking device 741 can include an optical localizer. Te optical localizer can be operated and be used to track the tracking device 500 by measuring light waves, timing, etc. from the tracking device 500. Optical tracking systems include the StealthStation® and StealthStation®Treon® sold by Medtronic, Inc. Therefore, the discussion of the tracking device 600, herein, will be understood to be directed to any appropriate tracking device, including EM, optical, acoustic, radar, etc.

The tracking device 600, either alone or in combination with the guide device, can be used by the tracking system 750 to determine the location of the guide apparatus 10, or the various portions thereof. For example, the tracking system 750 can be used to determine the location and orientation of the guide member 42 relative to a portion of the anatomy of the patient 728. As discussed further herein, this location and orientation can be illustrated on the display device 722.

Each of the tracking devices 600, 738, 762 can also be coupled to the navigation device interface 756 to forward the information to the coil array controller 754. For example, the dynamic reference frame 758, according to various embodiments, may include a small magnetic field detector as the tracking device 762. The dynamic reference frame 758 may be fixed to the patient 728 adjacent to the region being navigated so that any movement of the patient 728 is detected as relative motion between the transmitter coil array 752 and the dynamic reference frame 758. The dynamic reference frame 758 can be interconnected with the patient 728 in any appropriate manner, including those discussed herein. Any relative motion is forwarded to the coil array controller 754, which updates registration correlation and maintains accurate navigation, further discussed herein. An electromagnetic dynamic reference frame 758 can be configured as a pair or trio of orthogonally oriented coils, each having the same center or may be configured in any other non-coaxial or co-axial coil configurations.

The dynamic reference frame 758 may be affixed externally to the patient 728, adjacent to the region of navigation, such as on the patient's cranium, femur, tibia, humerus, etc., as shown in FIG. 11. The dynamic reference frame 758 can be affixed to the patient's skin, by way of a selected adhesive patch and/or a tensioning system. The dynamic reference frame 758 may also be removably attachable to a fiducial marker 769. The fiducial markers can be anatomical landmarks or members attached or positioned on the patient's 728 body. The dynamic reference frame 758 can also be connected to a bone portion of the anatomy. The bone portion can be adjacent the area of the procedure, the bone of the procedure, or any appropriate body portion.

Although the discussion above is directed to an electromagnetic navigation and tracking system, it will be understood that any appropriate tracking system can be used as the tracking system 750. For example, one skilled in the art will understand that appropriate tracking systems include, but are not limited to, an optical tracking system, a radar tracking system, an acoustic tracking system, an accelerometer tracking system. Nevertheless, the tracking system can include any appropriate portions, such as an appropriate localizer for the tracking system and appropriate tracking devices for the tracking system. Thus, the discussion herein regarding an electromagnetic tracking system is merely exemplary of any appropriate tracking system. Also, more than one tracking system can be used during a procedure, such as a hybrid system discussed above. Thus, an EM and an optical tracking system can be used at the same time to track a tracking device within the same space.

Briefly, the navigation system 700, according to various embodiments, operates as follows. The navigation system 700 creates a translation map between all points in the image data or image space and the corresponding points in the patient's anatomy in patient space, particularly if image data of the patient 728 is used. After this map is established, the image space and patient space are registered. In other words, registration is the process of determining how to correlate a position in image space with a corresponding point in real or patient space. This can also be used to illustrate a position of the guide apparatus 10 relative to the proposed trajectory and/or the determined anatomical target. The work station 742 in combination with the coil array controller 754 and the C-arm controller 734 identify the corresponding point on the pre-acquired image or atlas model relative to the tracked guide apparatus 10 and display the position on display device 722 and relative to the image data 723. This identification is known as navigation or localization. An icon representing the localized point or instruments is shown on the display device 722 within several two-dimensional image planes, as well as on three and four dimensional images and models.

To register the patient 728, the surgeon 721 may use point registration by selecting and storing particular points from the pre-acquired images and then touching the corresponding points on the patient's 728 anatomy with a pointer probe or any appropriate tracked device. The navigation system 700 analyzes the relationship between the two sets of points that are selected and computes a match, which allows for a determination of a correlation of every point in the image data or image space with its corresponding point on the patient's anatomy or the patient space.

The points that are selected to perform registration or form a translation map are the fiducial markers 769, such as anatomical or artificial landmarks. Again, the fiducial markers 769 are identifiable on the images and identifiable and accessible on the patient 728. The fiducial markers 769 can be artificial landmarks that are positioned on the patient 728 or anatomical landmarks that can be easily identified in the image data. The artificial fiducial markers 69, can also form part of the dynamic reference frame 758, such as those disclosed in U.S. Pat. No. 6,381,485, entitled "Registration of Human Anatomy Integrated for Electromagnetic Localization," issued Apr. 30, 2002, herein incorporated by reference. It will be understood that the "X" illustrated in FIG. 11 can merely indicate a position of a fiducial marker 769 rather than being the fiducial marker 769.

The system 700 may also perform registration using anatomic surface information or path information as is known in the art (and may be referred to as auto-registration). The system 700 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", incorporated herein by reference.

In order to maintain registration accuracy, the navigation system 700 can continuously track the position of the patient 728 during registration and navigation with the dynamic reference frame 758. This is because the patient 728, dynamic reference frame 758, and transmitter coil array 752 may all move during the procedure, even when this movement is not desired. Alternatively, the patient 728 may be held immobile once the registration has occurred, such as with a head frame. Therefore, if the navigation system 700 did not track the position of the patient 728 or area of the anatomy, any patient movement after image acquisition would result in inaccurate navigation within that image. The dynamic reference frame 758 allows the tracking system 750 to track the anatomy and can assist in registration. Because the dynamic reference frame 758 is rigidly fixed to the patient 728, any movement of the anatomy or the transmitter coil array 752 is detected as the relative motion between the transmitter coil array 752 and the dynamic reference frame 758. This relative motion is communicated to the coil array controller 754, via the navigation probe interface 756, which updates the registration correlation to thereby maintain accurate navigation.

The dynamic reference frame 758 can be affixed to any appropriate portion of the patient 728, and can be used to register the patient space to the image data or image space, as discussed above. For example, when a procedure is being performed relative to the femur 12, the dynamic reference frame 758 can be interconnected with the demur 12.

The navigation system 700 can detect both the position of the patient's anatomy and the position of the device 758 or attachment member (e.g. tracking device 600) attached to the guide apparatus 10. Knowing the location of these two items allows the navigation system 700 to compute and display the position of the guide apparatus 10 or any portion thereof in relation to the patient 728, after registration. The tracking system 750 is employed to track the guide apparatus 10 and the anatomy 728 simultaneously, as discussed above according to various embodiments.

To obtain maximum accuracy it can be selected to fix the dynamic reference frame 758 in each of at least 6 degrees of freedom. Thus, the dynamic reference frame 758 or any of the tracking sensors can be fixed relative to axial motion X, translational motion Y, rotational motion Z, yaw, pitch, and roll relative to the portion of the patient 728 to which it is attached. Any appropriate coordinate system can be used to describe the various degrees of freedom. Fixing the dynamic reference frame 758 relative to the patient 728 in this manner can assist in maintaining maximum accuracy of the navigation system 700.

When image data 723 is provided for display on the display device 722 then an icon 790 representing a location of the guide apparatus 10 can be displayed relative to it. The icon 780 can represent the entire guide apparatus 10 or any portion thereof, such as only the alignment block 42, according to various embodiments. It can be selected to display only the position of the alignment block 42 when the alignment block will be used to reference the position of the resection or the resection guide 650.

Other icons can also be displayed. For example, the bone contacting portion, according to various embodiments, can be used to determine planes for display of the display device 722. As discussed above, the surface 66 can be used to define a plane of the distal portion of the demur 12. Thus, an icon representing the plane of the distal end of the femur 12 can also be displayed. It will be understood, that any other plane or position relative to the guide apparatus 10 can also be displayed.

Alternatively, image data 723 need not be displayed. According to various embodiments, angles and other geographical representations can be displayed on the display device 722. In various embodiments, the position and orientation of the alignment block 42 can be displayed and can provide sufficient information to the user 721 to place the alignment pins 138 or perform a resection.

In addition, a surgical plan can be created and stored in the member 746. According to various embodiments, the plan can be used to assist in ensuring that the alignment block 42 is positioned in the appropriate location relative to the femur 12. The workstation 742 can provide feedback to the user 721 as the alignment block 42 is moved relative to the patient 728. Feedback can include auditory feedback, visual, tactile, etc. For example, an "planned" location icon can be displayed and a real time alignment block icon can be displayed. Thus, a user can move the alignment block 42 until the two icons overlap. At this point the guide apparatus can be locked in place and the resection made, as discussed above.

The icons on the display device can be used to illustrate a dynamic or moving portion. For example, the icons of the guide apparatus 10 or the alignment block 42 can be illustrated on the display device 722 as an icon that is moving. This moving icon can be used by the user 721 to determine the real time position of the tracked portion relative to another portion or the patient.

An icon can also be produced that illustrated the position of the cutting guide 650. For example, one of more cutting panes can be illustrated that can be produced by the cutting guide 650. The display device can display icons representing these various cutting planes. Further, the planes can be illustrated for viewing for the user 721 when placing the cutting guide 650.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A guide system comprising:
   a bone connection portion configured to be secured to a bone;
   a plate member coupled to the bone connection portion and configured to rotate about a first axis when the bone connection portion is secured to the bone;
   a rail portion coupled to the plate member and configured to rotate about a second axis when the bone connection portion is secured to the bone;
   an alignment block coupled to the rail portion and configured to move along a third axis when the bone connection portion is secured to the bone, wherein the alignment block defines a guide slot; and
   a tracking device, wherein a portion of the tracking device is removably arranged within the guide slot and is configured to allow a tracking system to track at least one of the plate member, the rail portion and the alignment block,
   wherein the first axis, second axis and third axis intersect with each other.

2. The guide system of claim 1, wherein:
   the bone connection portion includes a bone fixation portion and a guide member;
   the guide member is arranged substantially orthogonal to the bone fixation portion such that, when the bone connection portion is secured to the bone, (i) the bone fixation portion is arranged on a first side of the bone, and (ii) the guide member is arranged on a second side of the bone; and
   the second side is different than the first side.

3. The guide system of claim 2, wherein the plate member is in contact with the guide member of the bone connection portion.

4. The guide system of claim 1, wherein:
   the bone connection portion includes a projection member;
   the plate member defines a passage and is coupled to the bone connection portion by the projection member;
   the projection member extends into the passage; and
   the first axis extends through the passage.

5. The guide system of claim 1, further comprising a plate member locking assembly, configured to (i) while in a secured configuration, inhibit relative motion between the bone connection portion and the plate member, and (ii) while in an unsecured configuration, permit relative motion between the bone connection portion and the plate member.

6. The guide system of claim 1, wherein:
   the plate member defines a plurality of grooves;
   the rail portion includes a plurality of dowels;
   the rail portion is coupled to the plate member by the plurality of dowels; and
   the plurality of dowels are received within the grooves such that the second axis is defined by the plurality of dowels.

7. The guide system of claim 6, further comprising a rail portion locking assembly configured to (i) while in a secured configuration, inhibit relative motion between the plate member and the rail portion, and (ii) while in an unsecured configuration, permit relative motion between the plate member and the rail portion.

8. The guide system of claim 7, wherein:
   the rail portion includes a rail;
   the alignment block includes a plurality of extensions;
   the alignment block is coupled to the rail portion by the plurality of extensions; and
   the plurality of extensions are slidably received within the rail and allow the alignment block to be slid along the third axis and relative to the rail.

9. The guide system of claim 1, further comprising an alignment block locking assembly configured to (i) while in a secured configuration, inhibit relative motion between the rail portion and the alignment block, and (ii) while in an unsecured configuration, permit relative motion between the rail portion and the alignment block.

10. The guide system of claim 1, wherein:
    the rail portion further includes a rail;
    the alignment block includes a plurality of extensions;
    the alignment block is coupled to the rail portion by the plurality of extensions; and
    the plurality of extensions are slidably received within the rail and allow the alignment block to be slid along the third axis and relative to the rail.

11. The guide system of claim 10, further comprising an alignment block locking assembly configured to (i) while in a secured configuration, inhibit relative motion between the rail portion and the alignment block, and (ii) while in an unsecured configuration, permit relative motion between the rail portion and the alignment block.

12. The guide system of claim 1, further comprising the tracking system configured to utilize the tracking device to track:
    rotation of the plate member about the first axis;
    rotation of the rail portion about the second axis; and
    movement of the alignment block along the third axis.

13. The guide system of claim 1, wherein the first axis, second axis and third axis intersect with each other at a single point.

14. The guide system of claim 13, wherein the first axis, second axis and third axis are perpendicular to each other.

15. A guide system comprising:
    a bone connection portion configured to be secured to a bone;

a plate member coupled to the bone connection portion and configured to rotate about a first axis when the bone connection portion is secured to the bone;

a rail portion coupled to the plate member and configured to rotate about a second axis when the bone connection portion is secured to the bone; and an alignment block coupled to the rail portion and configured to move along a third axis when the bone connection portion is secured to the bone, wherein
the first axis, second axis and third axis intersect with each other, and
the alignment block comprises a bore for guiding a drill bit or an alignment pin (i) in a direction perpendicular to the third axis, and (ii) into the bone.

16. The guide system of claim 15, wherein:
the bone connection portion includes a bone fixation portion and a guide member;
the guide member is arranged substantially orthogonal to the bone fixation portion such that, when the bone connection portion is secured to the bone, (i) the bone fixation portion is arranged on a first side of the bone, and (ii) the guide member is arranged on a second side of the bone; and
the second side is different than the first side.

17. The guide system of claim 16, wherein the plate member is in contact with the guide member of the bone connection portion.

18. The guide system of claim 15, wherein:
the bone connection portion includes a guide member and a clamping plate;
the plate member includes a first portion and a second portion;
the first portion includes a first projection member;
the second portion includes a second projection member; and
the first projection member and the second projection member are positioned between the guide member and the clamping plate.

19. The guide system of claim 15, further comprising a plate member locking assembly configured to (i) while in a secured configuration, inhibit relative motion between the bone connection portion and the plate member, and (ii) while in an unsecured configuration, permit relative motion between the bone connection portion and the plate member.

20. The guide system of claim 15, wherein:
the plate member defines a plurality of grooves;
the rail portion includes a plurality of dowels;
the rail portion is coupled to the plate member by the plurality of dowels; and
the plurality of dowels are received within the grooves such that the second axis is defined by the plurality of dowels.

21. The guide system of claim 20, further comprising a rail portion locking assembly configured to (i) while in a secured configuration, inhibit relative motion between the plate member and the rail portion, and (ii) while in an unsecured configuration, permit relative motion between the plate member and the rail portion.

22. The guide system of claim 21, wherein:
the rail portion further includes a rail;
the alignment block includes a plurality of extensions;
the alignment block is coupled to the rail portion by the plurality of extensions; and
the plurality of extensions are slidably received within the rail and allow the alignment block to be slid along the third axis and relative to the rail.

23. The guide system of claim 15, further comprising an alignment block locking assembly, configured to (i) while in a secured configuration, inhibit relative motion between the rail portion and the alignment block, and (ii) while in an unsecured configuration, permit relative motion between the rail portion and the alignment block.

24. The guide system of claim 15, wherein the first axis, second axis and third axis intersect with each other at a single point.

25. The guide system of claim 24, wherein the first axis, second axis and third axis are perpendicular to each other.

26. A method comprising:
securing a bone connection portion to a bone;
rotating a plate member coupled to the bone connection portion about a first axis while the bone connection portion is secured to the bone;
securing the plate member to the bone connection portion such that relative movement between the plate member and bone connection portion is inhibited;
rotating a rail portion coupled to the plate member about a second axis while the bone connection portion is secured to the bone;
securing the rail portion to the plate member such that relative movement between the rail portion and plate member is inhibited;
moving an alignment block, coupled to the rail portion, along a third axis while the bone connection portion is secured to the bone, wherein the alignment block comprises a guide slot;
securing the alignment block to the rail portion such that relative movement between the alignment block and the rail portion is inhibited;
sliding a portion of a tracking device in the guide slot; and
tracking a location of at least one of the plate member, the rail portion and the alignment block,
wherein the first axis, second axis and third axis intersect with each other.

27. The method of claim 26, further comprising:
tracking rotation of the plate member about the first axis;
tracking rotation of the rail portion about the second axis; and
tracking movement of the alignment block along the third axis.

28. The method of claim 26, wherein the tracking of the location of the at least one of the plate member, the rail portion and the alignment block includes utilizing a tracking system to track the tracking device.

29. A method comprising:
securing a bone connection portion to a bone;
rotating a plate member coupled to the bone connection portion about a first axis while the bone connection portion is secured to the bone;
securing the plate member to the bone connection portion such that relative movement between the plate member and bone connection portion is inhibited;
rotating a rail portion coupled to the plate member about a second axis while the bone connection portion is secured to the bone;
securing the rail portion to the plate member such that relative movement between the rail portion and plate member is inhibited;
moving an alignment block, coupled to the rail portion, along a third axis while the bone connection portion is secured to the bone, wherein the first axis, second axis and third axis intersect with each other, wherein a tracking device is slidably positioned within a slot defined by the alignment block;

securing the alignment block to the rail portion such that relative movement between the alignment block and the rail portion is inhibited;

tracking a location of at least one of the plate member, the rail portion and the alignment block;

removing the tracking device from the slot after securing the plate member to the bone connection portion, securing the rail portion to the plate member, and securing the alignment block to the rail portion; and inserting a resection device within the slot to resect a portion of the bone or other portion of an anatomy of a subject.

30. The method of claim 26, wherein the first axis, second axis and third axis intersect with each other at a single point.

31. The method of claim 28, wherein the first axis, second axis and third axis are perpendicular to each other.

32. The method of claim 26, further comprising displaying the first axis, second axis and third axis on a display.

33. The guide system of claim 1, wherein the tracking device comprises:

the portion of the tracking device;

an arm connected to the portion of the tracking device; and a plurality of optical tracking portions connected to the arm and configured to be tracked by the tracking system.

34. The guide system of claim 15, wherein:

the alignment block comprises a plurality of bores; and each of the plurality of bores is configured to guide the drill bit or the alignment pin into the bone.

35. The guide system of claim 15, wherein the alignment block is arranged relative to the plate member and the rail portion to guide the drill bit or the alignment pin through slots in the plate member and the rail portion.

36. The guide system of claim 16, wherein the alignment block is arranged relative to the plate member and the rail portion to guide the drill bit or the alignment pin through slots in the plate member, the rail portion and the guide member.

37. The method of claim 26, further comprising tracking a plurality of optical tracking portions, wherein the tracking device comprises:

the portion of the tracking device;

an arm connected to the portion of the tracking device; and the plurality of optical tracking portions connected to the arm.

* * * * *